ание

United States Patent
Schiltz et al.

(10) Patent No.: US 11,981,678 B2
(45) Date of Patent: May 14, 2024

(54) SUBSTITUTED [1,2,4]TRIAZOLO[4,3-C]PYRIMIDIN-5-AMINES AND PROTEOLYSIS-TARGETING CHIMERIC DERIVATIVES THEREOF (PROTACS) THAT INDUCE DEGRADATION OF EMBRYONIC ECTODERM DEVELOPMENT (EED) PROTEIN

(71) Applicant: Northwestern University, Evanston, IL (US)

(72) Inventors: Gary E. Schiltz, Naperville, IL (US); Jindan Yu, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 17/733,752

(22) Filed: Apr. 29, 2022

(65) Prior Publication Data

US 2022/0372039 A1    Nov. 24, 2022

Related U.S. Application Data

(60) Provisional application No. 63/201,434, filed on Apr. 29, 2021.

(51) Int. Cl.
 *A61K 31/519* (2006.01)
 *C07D 487/04* (2006.01)

(52) U.S. Cl.
 CPC .................. *C07D 487/04* (2013.01)

(58) Field of Classification Search
 CPC .......................... A61K 31/519; C07D 487/04
 USPC ....................................... 514/262.1; 544/263
 See application file for complete search history.

(56) References Cited

U.S. PATENT DOCUMENTS

| | | |
|---|---|---|
| 2018/0085465 A1 | 3/2018 | Bradner et al. |
| 2018/0134684 A1 | 5/2018 | Bradner et al. |
| 2018/0186785 A1 | 7/2018 | Crews et al. |
| 2018/0327419 A1 | 11/2018 | Bradner et al. |
| 2019/0016703 A1 | 1/2019 | Gray et al. |
| 2019/0071415 A1 | 3/2019 | Bradner et al. |
| 2019/0076539 A1 | 3/2019 | Phillips et al. |
| 2019/0076540 A1 | 3/2019 | Phillips et al. |
| 2019/0076541 A1 | 3/2019 | Phillips et al. |
| 2019/0076542 A1 | 3/2019 | Phillips et al. |
| 2019/0106417 A1 | 4/2019 | Gray et al. |
| 2019/0151295 A1 | 5/2019 | Crew et al. |
| 2019/0151457 A1 | 5/2019 | Bradner et al. |
| 2019/0194190 A1 | 6/2019 | Yang et al. |
| 2019/0262502 A1 | 8/2019 | Garcia-Gareta et al. |
| 2019/0263798 A1 | 8/2019 | Harling et al. |
| 2019/0275161 A1 | 9/2019 | Heightman et al. |
| 2020/0022966 A1 | 1/2020 | Tang et al. |
| 2020/0085817 A1 | 3/2020 | Jaenisch et al. |
| 2020/0102298 A1 | 4/2020 | Gray et al. |
| 2020/0140456 A1 | 5/2020 | Phillips et al. |

FOREIGN PATENT DOCUMENTS

WO   WO-2020162725 A1 *   8/2020   ........... A61K 31/519

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
An et al., "Small-molecule PROTACs: An emerging and promising approach for the development of targeted therapy drugs," EBioMedicine. Oct. 2018; 36: 553-562.
Gu et al., "PROTACs: An Emerging Targeting Technique for Protein Degradation in Drug Discovery," Bioessays. Apr. 2018; 40(4):e1700247.
Nalawansha et al., "PROTACs: An emerging therapeutic modality in precision medicine," Cell Chemical Biology, vol. 27, Issue 1, 2020, pp. 41-46.e17.
Potjewyd et al., "Degradation of Polycomb Repressive Complex 2 with an EED-Targeted Bivalent Chemical Degrader," Cell Chem. Biol. 2020, 27 (1), 47-56.
Wang et al., "A covalently bound inhibitor triggers EZH2 degradation through CHIP-mediated ubiquitination," EMBO J. May 2, 2017; 36(9): 1243-1260.

\* cited by examiner

*Primary Examiner* — Douglas M Willis

(74) *Attorney, Agent, or Firm* — Quarles & Brady LLP

(57) ABSTRACT

Disclosed are compounds that bind to embryonic ectoderm development (EED) protein and proteolysis-targeting chimeric (PROTAC) derivatives thereof that induce degradation of EED. The disclosed compounds may be characterized as substituted [1,2,4]triazolo[4,3-c]pyrimidin-5-amine compounds. The disclosed PROTAC derivatives thereof typically include a first targeting moiety that binds to EED ($M_{EED}$) which may be derived from the disclosed [1,2,4]triazolo[4,3-c]pyrimidin-5-amine compounds that bind to EED. The first targeting moiety typically is linked via a bond or a linker (L) to a second targeting moiety that binds to an E3 ubiquitin ligase ($M_{E3}$). As such, the disclosed PROTACS may be described as having a formula $M_{EED}$-L-$M_{E3}$ or $M_{E3}$-L-$M_{EED}$, wherein $M_{EED}$ has a formula of

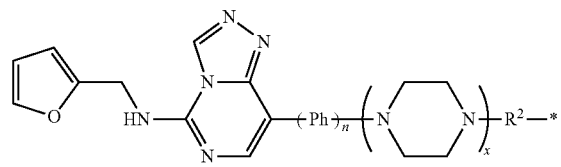

where $R^2$, n, and x are as described herein.

4 Claims, 4 Drawing Sheets

SUBSTITUTED [1,2,4]TRIAZOLO[4,3-C]PYRIMIDIN-5-AMINES AND PROTEOLYSIS-TARGETING CHIMERIC DERIVATIVES THEREOF (PROTACS) THAT INDUCE DEGRADATION OF EMBRYONIC ECTODERM DEVELOPMENT (EED) PROTEIN

CROSS-REFERENCE TO RELATED APPLICATIONS

The present application claims priority to U.S. Provisional Patent Application No. 63/201,434, filed Apr. 29, 2021, the entire contents of which are hereby incorporated by reference.

STATEMENT REGARDING FEDERALLY SPONSORED RESEARCH

This invention was made with government support under W81XWH-17-1-0405 and W81XWH-17-1-0406 awarded by U.S. Army Medical Research and Materiel Command. The government has certain rights in the invention.

BACKGROUND OF THE INVENTION

The field of the invention relates to compounds that bind to embryonic ectoderm development (EED) protein and proteolysis-targeting chimeric derivatives thereof (PROTACs) that induce degradation EED. In particular, the field of the invention relates to substituted [1,2,4]triazolo[4,3-c]pyrimidin-5-amine compounds and PROTAC derivatives thereof that target the EED for degradation. The disclosed compounds and PROTAC derivates thereof may be utilized for the treatment of diseases and disorders associated with the activity of EED such as cell proliferation diseases and disorders including cancer.

The protein EED is an essential component of the polycomb repressive complex 2 (PRC2). The PRC2 complex functions in epigenetic silencing via methylation, and EED promotes allosteric activation of the methyltransferase activity of PRC2. PRC2 target genes include transcription factors, signaling genes for development, and tumor suppressor genes, all of which are implicated in uncontrolled cell development. As such, proteins of the PRC2 complex, including EED, are potential targets for therapeutic agents for treating cancer. This protein is a methyltransferase enzyme that produces trimethylation of histone H3 lysine 27 (H3K27me3).

Aberrant EZH2 leads to tumor growth and is a well-validated target in a variety of cancers. For EZH2 to be catalytically active, it must be part of a functional and intact PRC2 complex. The PRC2 complex also provides stability to EZH2 and reduces its turnover in the cell. In addition to its enzymatic function, EZH2 is also able to increase tumor cell proliferation in a non-enzymatic manner. Because of this, enzyme inhibitors may not fully abolish all of its oncogenic functions. Disruption of the PRC2 complex or preventing its formation is expected to block the ability of EZH2 to catalyze methyltransferase activity as well as lead to increased EZH2 protein degradation.

Proteolysis-targeting chimeric molecules (PROTACs) are an emerging technology that may be utilized to target previously "undruggable" targets, such as transcription factors and non-enzymatic proteins. (See, e.g., An et al., "Small-molecule PROTACs: An emerging and promising approach for the development of targeted therapy drugs," EBioMedicine. 2018 October; 36: 553-562; and Gu et al., "PROTACs: An Emerging Targeting Technique for Protein Degradation in Drug Discovery," Bioessays. 2018 April; 40(4):e1700247, the contents of which are incorporated herein by reference in their entireties). PROTACs are chimeric molecules that may be characterized as "heterobifunctional" in that PROTACs include a ligand for recruiting an E3 ubiquitin ligase, a linker, and another ligand to bind with the protein targeted for degradation. Designed as such, PROTACs "hijack" the E3 ubiquitin ligase to the protein which is targeted for protein degradation via ubiquitination, even if the targeted protein is not a physiological substrate for degradation via the ubiquitin-proteasome system.

Here, we disclose compounds that bind EED. The disclosed compounds may be derivatized to form PROTACs that induce degradation of EED.

BRIEF SUMMARY OF THE INVENTION

Disclosed are compounds that bind to embryonic ectoderm development (EED) protein and proteolysis-targeting chimeric derivatives thereof (PROTACs) that induce degradation EED. The disclosed compounds and PROTACs may be utilized as EED targeting agents.

The disclosed compounds may be characterized as substituted [1,2,4]triazolo[4,3-c]pyrimidin-5-amine compounds. The disclosed compounds may be utilized for binding to EED and further may be derivatized to form proteolysis-targeting chimeric molecules (PROTACs) that target EED for degradation. The disclosed compounds and PROTACs may be used in pharmaceutical compositions and methods for treating cell proliferative disorders associated with EED activity, such as cancer.

The disclosed compounds may include substituted [1,2,4]triazolo[4,3-c]pyrimidin-5-amine compounds having a Formula I:

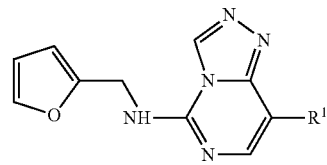

wherein
$R^1$ is hydrogen or $R^1$ has a formula:

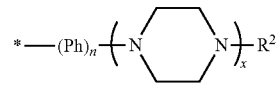

wherein
Ph is phenyl;
n is 0 or 1;
x is 0 or 1; and
$R^2$ is hydrogen, alkyl, alkoxy, —C(O)—H, —C(O)—$(CH_2)_m$—$CH_3$ where m is 0-20, —C(O)—$(CH_2CH_2O)_n$—H or —C(O)—$(CH_2CH_2O)_n$—$CH_3$ where m is 1-20, —C(O)—$CH_2OCH_3$, —C(O)—$CH_2$, —CH$(CH_2CH_2CH_3)_2$, —S(O)(O)—H, or —S(O)(O)—$CH_3$.

The disclosed compounds may exhibit one or more biological activities. The disclosed compounds may inhibit one or more biological activities of EED protein (e.g., the disclosed compounds may inhibit binding of EED to enhancer zeste homolog 2 (EZH2) protein). The disclosed compounds may inhibit the growth of cells that express EED protein (preferably by at least about 10%, 20%, 30%, 40%, or 50%, at a concentration of less than about 100 µM, 50 µM, 10 µM, 1 µM, 0.1 µM, 0.05 µM, 0.01 µM, 0.005 µM, 0.001 µM, or less). The disclosed compounds may not inhibit the growth of cells that do not express EED protein (preferably at a concentration of greater than about 0.001 µM, 0.005 µM, 0.01 µM, 0.5 µM, 0.1 µM, 1.0 µM, M, and 100 µM or higher).

The disclosed compounds may be derivatized to form PROTACS that induce degradation of EED. The disclosed PROTACs may comprise a moiety that binds to EED that is covalently attached to a moiety that binds to a ubiquitin ligase. In some embodiments, the disclosed PROTACs include a first targeting moiety that binds to EED ($M_{EED}$) which may be derived from a substituted [1,2,4]triazolo[4,3-c]pyrimidin-5-amine compound. The first targeting moiety may be covalently attached via a bond or a linker (L) to a second targeting moiety that binds to a ubiquitin ligase such as an E3 ubiquitin ligase ($M_{E3}$). As such, the disclosed PROTACS may be described as having a formula $M_{EED}$-L-$M_{E3}$ or $M_{E3}$-L-$M_{EED}$.

The disclosed PROTACs preferably target the E3 ubiquitin ligase moiety to EED which subsequently is ubiquitinated and targeted for degradation. The disclosed PROTACs may be utilized for the treatment of diseases and disorders associated with the biological activity of EED such as cell proliferation diseases and disorders including cancer.

The EED targeting moiety of the disclosed PROTACs ($M_{EED}$) typically is linked via a bond or a linker (L) to a second targeting moiety that binds to an E3 ubiquitin ligase ($M_{E3}$). The EED targeting moiety may comprise a radicalized form of a compound of a Formula I, for example wherein the EED moiety is attached to the linker via a radicalized form of substituent $R^1$ of Formula I.

Suitable linkers for the disclosed PROTACs may include, but are not limited to linkers comprising an alkyl moiety and/or a polyethylene glycol moiety. Other suitable linkers for the disclosed PROTACS may include an alkyl moiety, an alkylalkyne moiety, and/or an aminoalkyl alkyne moiety.

The E3 ubiquitin ligase targeting moiety of the disclosed PROTACs ($M_{E3}$) typically binds and/or targets the PROTACs to an E3 ubiquitin ligase. Suitable E3 ubiquitin ligases may include, but are not limited to, Von Hippel-Lindau (VHL) E3 ubiquitin ligase, cereblon (CRBN) E3 ubiquitin ligase, inhibitor of apoptosis protein (IAP) E3 ubiquitin ligase, and mouse double minute 2 homolog (MDM2) E3 ubiquitin ligase.

The E3 ubiquitin ligase targeting moiety of the disclosed PROTACs ($M_{E3}$) typically is derived from a compound that binds to an E3 ubiquitin ligase, for example, as a ligand for an E3 ubiquitin ligase. Suitable ligands may include, but are not limited to, ligands derived from thalidomide, pomalidomide, lenalidomide, VHL ligand 1 (VHL-1), VHL ligand 2 (VHL-2), VH032, VL-269, LCL161, hydroxyproline-based ligands, and HIF-1α-derived (R)-hydroxyproline, including radicalized forms.

The disclosed PROTACs may exhibit one or more biological activities. The disclosed PROTACs may inhibit the growth of cells that express EED (preferably by at least about 10%, 20%, 30%, 40%, or 50%, at a concentration of less than about 100 µM, 50 µM, 10 µM, 1 µM, 0.1 µM, 0.05 µM, 0.01 µM, 0.005 µM, 0.001 µM, or less). The disclosed PROTACs may not inhibit the growth of cells that do not express EED (preferably at a concentration of greater than about 0.001 µM, 0.005 µM, 0.01 µM, 0.5 µM, 0.1 µM, 1.0 µM, 10 µM, and 100 µM or higher).

Also disclosed are pharmaceutical compositions comprising the disclosed compounds and PROTAC derivatives thereof and a suitable pharmaceutical carrier, excipient, or diluent. The disclosed pharmaceutical compositions may comprise an effective amount of the compound or PROTAC derivative thereof for inhibiting the growth of cancer cells when administered to a subject in need thereof.

Also disclosed are methods for treating cell proliferation diseases and disorders such as cancer. The methods may include administering the disclosed compounds or PROTAC derivatives thereof or pharmaceutical compositions comprising the disclosed compounds or PROTAC derivatives thereof to a subject in need thereof, for example, to a subject having cancer. The disclosed compounds and PROTAC derivatives thereof or pharmaceutical compositions comprising the disclosed compounds and PROTAC derivatives thereof may be administered with additional therapeutic agents, optionally in combination, in order to treat cell proliferative diseases and disorders. Cell proliferative diseases and disorders treated by the disclosed methods may include, but are not limited to, cancers selected from the group consisting of multiple myeloma, leukemia, non-small cell lung cancer, colon cancer, cancer of the central nervous system, melanoma, ovarian cancer, renal cancer, prostate cancer, and breast cancer.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

References to the compounds in the drawings is done by the last four digits of the name shown in the Tables.

DETAILED DESCRIPTION OF THE INVENTION

Figure 1:
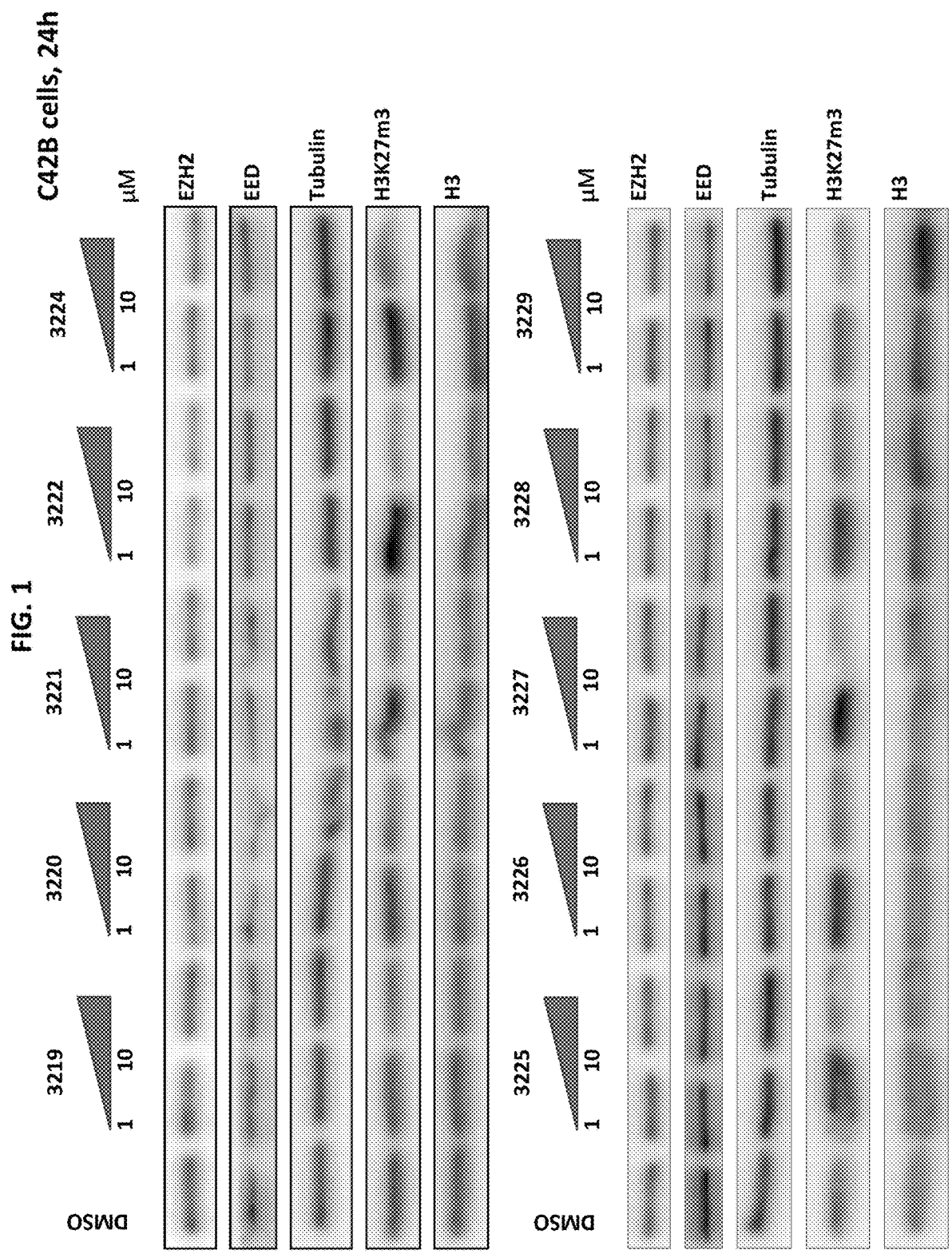
FIG. 1 shows western blots (WB) comparing of activity of compounds 3219, 3220, 3221, 3222, 3224, 3225, 3226, 3227, 3228, and 3229 against EZH2, EED, trimethylation of histone H3 lysine 27 (H3k27me3), and histone H3. C4-2B cells were treated with indicated compounds for 24 hours with indicated doses before WB analyses.

The present invention is described herein using several definitions, as set forth below and throughout the application.

Unless otherwise specified or indicated by context, the terms "a", "an", and "the" mean "one or more." For example, "a compound" and "a substituent" and a "moiety" and a "PROTAC" should be interpreted to mean "one or more compounds" and "one or more substituents" and "one or more moieties" and "one or more PROTACs", respectively.

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

As used herein, a "subject" may be interchangeable with "patient" or "individual" and means an animal, which may be a human or non-human animal, in need of treatment.

A "subject in need of treatment" may include a subject having a disease, disorder, or condition that is responsive to therapy with a compound that inhibits the biological activity of EED. Biological activities of EED which are inhibited by the disclosed compounds may include binding of EED to enhancer zeste homolog 2 (EZH2) protein.

A "subject in need of treatment" may include a subject having a disease, disorder, or condition that is responsive to therapy with a proteolysis-targeted chimeric molecule (PROTAC) that targets EED and induces degradation of EED, for example via ubiquitinization.

A "subject in need of treatment" may include a subject having a disease, disorder, or condition that is associated with EZH2 that is response to therapy with a compound that inhibits the biological activity of EED or that targets EED and induces degradation of EED.

A "subject in need of treatment" may include a subject having a cell proliferative disease, disorder, or condition such as cancer (e.g., cancers such as multiple myeloma, leukemia, non-small cell lung cancer, colon cancer, cancer of the central nervous system, melanoma, ovarian cancer, renal cancer, prostate cancer, and breast cancer). A "subject in need of treatment" may include a subject having a cell proliferative disease, disorder, or condition such as cancer that is associated with EED activity and/or that may be treated by administering an effective amount of an agent that modulates EED activity or that induces degradation of EED.

As used herein, the phrase "effective amount" shall mean that drug dosage that provides the specific pharmacological response for which the drug is administered in a significant number of subject in need of such treatment. An effective amount of a drug that is administered to a particular subject in a particular instance will not always be effective in treating the conditions/diseases described herein, even though such dosage is deemed to be a therapeutically effective amount by those of skill in the art.

As used herein, the term "modulate" means decreasing or inhibiting activity and/or increasing or augmenting activity. For example, modulating EED activity may mean increasing or augmenting EED activity and/or decreasing or inhibiting EED activity. The disclosed compounds and PROTACs may be administered to modulate EED activity (e.g., in a cell).

Chemical Entities New chemical entities and uses for chemical entities are disclosed herein. The chemical entities may be described using terminology known in the art and further discussed below.

As used herein, an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of straight-chain or branched alkyl group (i.e., a diradical of straight-chain or branched C1-C6 alkyl group). Exemplary alkylene groups include, but are not limited to —CH$_2$—, —CH$_2$CH$_2$—, —CH$_2$CH$_2$CH$_2$—, —CH(CH$_3$)CH$_2$—, —CH$_2$CH(CH$_3$)CH$_2$—, —CH(CH$_2$CH$_3$)CH$_2$—, and the like.

The term "haloalkyl" refers to an alkyl group that is substituted with at least one halogen. For example, —CH$_2$F, —CHF$_2$, —CF$_3$, —CH$_2$CF$_3$, —CF$_2$CF$_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxy" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido or carboxyamido (or amidocarboxyl), amidino, amino, aryl, arylalkyl, azido, carbamate, carbonate, carboxy, cyano, cycloalkyl, ester, ether, formyl, halo, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloheteroalkyl" refers to a monovalent saturated cyclic, bicyclic, or bridged cyclic hydrocarbon group of 3-12, 3-8, 4-8, or 4-6 carbons in which at least one carbon of the cycloalkane is replaced with a heteroatom such as, for example, N, O, and/or S.

The term "cycloalkylene" refers to a cycloalkyl group that is unsaturated at one or more ring bonds.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido or carboxyamido (or amidocarboxyl), amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido or carboxyamido (or amidocarboxyl), carboxylic acid, —C(O) alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3-to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines (e.g., mono-substituted amines or di-substituted amines), wherein substituents may include, for example, alkyl, cycloalkyl, heterocyclyl, alkenyl, and aryl.

The terms "alkoxy" or "alkoxyl" are art-recognized and refer to an alkyl group, as defined above, having an oxygen radical attached thereto. Representative alkoxy groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

The term "carbonyl" as used herein refers to the radical —C(O)—.

The term "oxo" refers to a divalent oxygen atom —O—.

The term "carboxamido" as used herein refers to the radical —C(O)NRR', where R and R' may be the same or different. R and R', for example, may be independently hydrogen, alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" or "amidyl" as used herein refers to a radical of the form —R$^1$C(O)N(R$^2$)—, —R$^2$C(O)N(R$^2$)R$^3$—, —C(O)NR$^2$R$^3$, or —C(O)NH$_2$, wherein R$^1$, R$^2$ and R$^3$, for example, are each independently hydrogen, alkyl, alkoxy, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds and molecules (e.g., PROTACs) of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds and molecules may be designated by the symbols "R" or "S," "+" or "−" depending on the configuration of substituents around the stereogenic carbon atom and or the optical rotation observed. The present invention encompasses various stereo isomers of these compounds and molecules and mixtures thereof. Stereoisomers include enantiomers and diastereomers.

Mixtures of enantiomers or diastereomers may be designated (±)" in nomenclature, but the skilled artisan will recognize that a structure may denote a chiral center implicitly. It is understood that graphical depictions of chemical structures, e.g., generic chemical structures, encompass all stercoisomeric forms of the specified compounds and molecules, unless indicated otherwise. Also contemplated herein are compositions comprising, consisting essentially of, or consisting of an enantiopure compound, which composition may comprise, consist essential of, or consist of at least about 50%, 60%, 70%, 80%, 90%, 95%, 96%, 97%, 98%, 99%, or 100% of a single enantiomer of a given compound (e.g., at least about 99% of an R enantiomer of a given compound).

The formulae of the compounds and molecules disclosed herein should be interpreted as encompassing all possible stereoisomers, enantiomers, or epimers of the compounds and molecules unless the formulae indicates a specific stereoisomer, enantiomer, or epimer. The formulae of the compounds and molecules disclosed herein should be interpreted as encompassing salts, esters, amides, or solvates thereof of the compounds and molecules. Substituted [1,2,4]Triazolo[4,3-c]Pyrimidin-5-Amine Compounds and Proteolysis-Targeting Chimeric Derivatives Thereof (PROTACs) that Induce Degradation of Embryonic Ectoderm Development (EED) Protein Disclosed are inhibitors of embryonic ectoderm development (EED) protein which may be utilized as EED targeting agents. The disclosed compounds may be characterized as substituted [1,2,4]triazolo[4,3-c]pyrimidin-5-amine compounds. The disclosed compounds may be utilized as inhibitors of EED and further may be derivatized to form proteolysis-targeting chimeric molecules (PROTACs) that target EED for degradation. The disclosed compounds and PROTACs may be used in pharmaceutical compositions and methods for treating cell proliferative disorders associated with EED activity, such as cancer.

In some embodiments, the disclosed compounds may have a Formula I or a salt, hydrate, or solvate thereof:

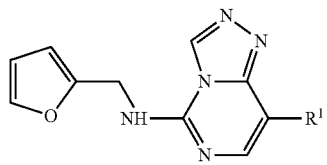

I wherein
$R^1$ is hydrogen or $R^1$ has a formula:

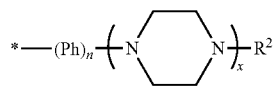

wherein
Ph is phenyl;
n is 0 or 1;
x is 0 or 1; and
$R^2$ is hydrogen, alkyl, alkoxy, —C(O)—H, —C(O)—(CH$_2$)$_n$—CH$_3$ where m is 0-20, —C(O)—(CH$_2$CH$_2$O)$_n$—H or —C(O)—(CH$_2$CH$_2$O)$_n$—CH$_3$ where m is 1-20, —C(O)—CH$_2$OCH$_3$, —C(O)—CH$_2$, —CH(CH$_2$CH$_2$CH$_3$)$_2$, —S(O)(O)—H, or —S(O)(O)—CH$_3$.

In some embodiments, $R^1$ is selected from:

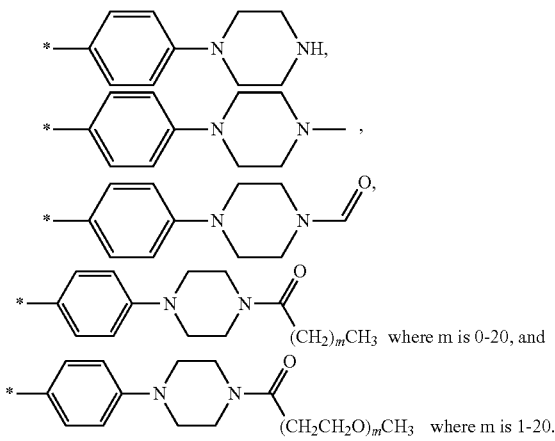

In some embodiments, $R^1$ is selected from:

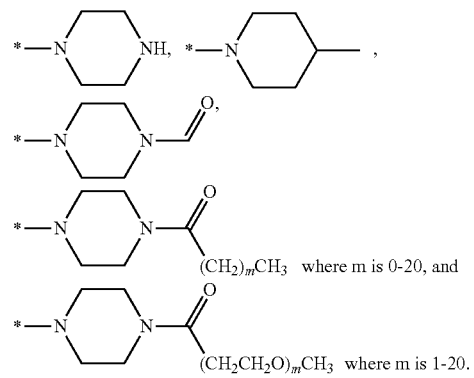

Also disclosed herein are proteolysis-targeted chimeric molecules (PROTACs) that induce degradation of EED protein. In some embodiments, the disclosed molecules may be described as having a formula: $M_{EED}$-L-$M_{E3}$ or alternatively $M_{E3}$-L-$M_{EED}$, wherein $M_{EED}$ is a moiety that binds to EED such as the compounds disclosed herein, L is a bond or a linker covalently attaching $M_{EED}$ and $M_{E3}$, and $M_{E3}$ is a moiety that binds to an E3 ubiquitin ligase.

In some embodiments of the disclosed PROTACS, $M_{EED}$ has a formula derived from a compound having a Formula I as per the disclosed compounds above or a radicalized or functionalized form thereof. In some embodiments of the disclosed PROTACS, $M_{EED}$ has a Formula II

II

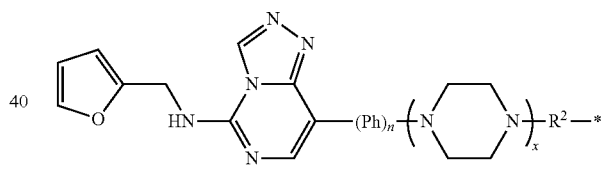

wherein
Ph is phenyl;
n is 0 or 1;
x is 0 or 1; and
$R^2$ is a bond or carbonyl.

In some embodiments, of the disclosed PROTACS, $M_{EED}$ has a formula selected from:

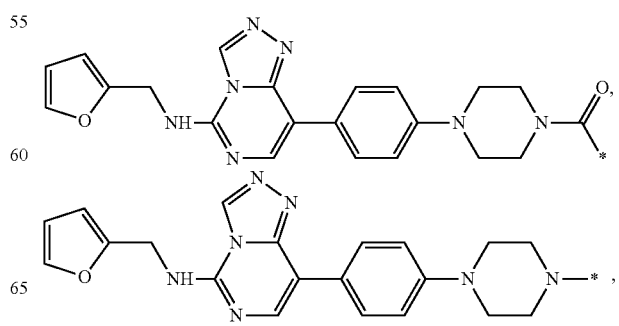

-continued

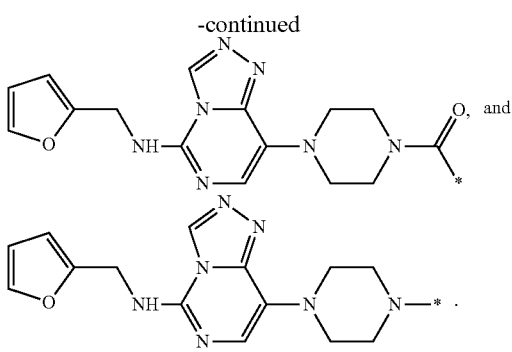

The disclosed PROTACs may include a bond or a linker (L) that conjugates the EED binding moiety ($M_{EED}$) and the E3 ubiquitin ligase binding moiety ($M_{E3}$). The PROTAC linker connects the functional moieties of a PROTAC, a target protein binder and an E3 ligase recruiter. Linkers used in the development of PROTACs include polyethylene glycol (PEG) linkers, Alkyl-Chain linkers, and Alkyl/ether linkers. Other PROTAC linkers may include those linkers described in one or more of U.S. Publication Nos. 2020/0140456; 2020/0102298; 2020/0085817; 2020/0022966; 2019/0275161; 2019/0263798; 2019/0262502; 2019/0194190; 2019/0151457; 2019/0151295; 2019/0106417; 2019/0076542; 2019/0076541; 2019/0076540; 2019/0076539; 2019/0071415; 2019/0016703; 2018/0327419; 2018/0186785; 2018/0134684; and 2018/0085465; the contents of which are incorporated herein by reference in their entireties.

In some embodiments, of the disclosed PROTACS, L comprises a polyethylene glycol moiety, an alkylalkyne moiety, and/or an aminoalkyl alkyne moiety.

In some embodiments of the disclosed PROTACs, L has a formula selected from: —(CH$_2$)$_m$—, —(CH$_2$)$_m$CH$_2$CH$_2$C(O)NHCH$_2$CH$_2$—, —(CH$_2$)$_m$CH$_2$CH$_2$C(O)NHCH$_2$CH$_2$CH$_2$—, —(CH$_2$CH$_2$O)$_n$CH$_2$CH$_2$C(O)NHCH$_2$CH$_2$—, —(CH$_2$CH$_2$O)$_n$CH$_2$CH$_2$C(O)NHCH$_2$CH$_2$CH$_2$—, —(CH$_2$CH$_2$O)$_n$CH$_2$CH$_2$—, —(CH$_2$CH$_O$)$_n$CH$_2$—, —(CH$_2$)$_m$C(O)NHCH$_2$CH$_2$—, —(CH$_2$CH$_2$O)$_n$CH$_2$CH$_2$C(O)NHCH$_2$CH$_2$—, —CH$_2$CH$_2$C(O)NHCH$_2$CH$_2$CH$_2$—, —CH$_2$CH$_2$C(O)NHCH$_2$CH$_2$CH$_2$C(O)NHCH$_2$CH$_2$—, —CH$_2$CH$_2$C(O)NHCH$_2$CH$_2$C(O)NHCH$_2$CH$_2$CH$_2$C(O)NHCH$_2$CH$_2$, —CH$_2$CH$_2$C(O)NHCH$_2$CH$_2$CH$_2$C(O)NHCH$_2$CH$_2$CH$_2$C(O)NHCH$_2$CH$_2$CH$_2$, —(CH$_2$CH$_2$O)$_n$CH$_2$CH$_2$—, —CH$_2$O(CH$_2$)$_m$—, —CH$_2$OCH$_2$C(O)NHCH$_2$CH$_2$—, —CH$_2$OCH$_2$C(O)NHCH$_2$CH$_2$CH$_2$—, and —CH$_2$OCH$_2$C(O)NHCH$_2$CH$_2$CH$_2$C(O)NHCH$_2$CH$_2$—, —CH$_2$OCH$_2$C(O)NHCH$_2$CH$_2$CH$_2$C(O)NHCH$_2$CH$_2$CH$_2$—, wherein m and n are 0-20.

The disclosed PROTACs typically include a moiety that binds to an E3 ubiquitin ligase ($M_{E3}$), for example, as a ligand for the E3 ubiquitin ligase ($M_{E3}$). Ligands for E3 ubiquitin ligases for use in preparing PROTACs are known in the art. (See, e.g., An et al., "Small-molecule PROTACs: An emerging and promising approach for the development of targeted therapy drugs," EBioMedicine. 2018 October; 36: 553-562; and Gu et al., "PROTACs: An Emerging Targeting Technique for Protein Degradation in Drug Discovery," Bioessays. 2018 April; 40(4):e1700247, the contents of which are incorporated herein by reference in their entireties).

In some embodiments of the disclosed PROTACs, $M_{E3}$ is a moiety that binds to an E3 ubiquitin ligase selected from Von Hippel-Lindau (VHL) E3 ubiquitin ligase, cereblon (CRBN) E3 ubiquitin ligase, inhibitor of apoptosis protein (IAP) E3 ubiquitin ligase, and mouse double minute 2 homolog (MDM2) E3 ubiquitin ligase.

In other embodiments of the disclosed PROTACs, $M_{E3}$ is a moiety derived from thalidomide, pomalidomide, lenalidomide, iberdomide, (S,R,S)-AHPC-Me hydrochloride, (S,R,S)-AHPC-Me dihydrochloride, cereblon modulator 1, thalidomide-propargyl, (S,R,S)-AHPC-propargyl, (S,R,S)-AHPC hydrochloride, CC-885, thalidomide-O—COOH, lenalidomide hemihydrate, thalidomide fluoride, thalidomide-OH, lenalidomide-Br, thalidomide D4, lenalidomide hydrochloride, (S,R,S)-AHPC-Me, cIAP1 ligand 1, TD-106, E3 ligase Ligand 8, E3 ligase Ligand 9, E3 ligase Ligand 10, E3 ligase Ligand 13, E3 ligase Ligand 14, E3 ligase Ligand 18, BC-1215, VHL ligand 1 (VHL-1), VHL ligand 2 (VHL-2), VHL Ligand 8 (VHL-8), VH032, VH032-cyclopropane-F, VH032 thiol, VH-298, VL-269, VL-285, LCL161, hydroxyproline-based ligands, HIF-1α-derived (R)-hydroxyproline, Nutlin carboxylic acid, (4R,5S)-Nutlin carboxylic acid, (S,R,S)-AHPC-Boc, AR antagonist 1, NV03, (S,R,S)-AHPC TFA, (S,R,S)-AHPC, β-Naphthoflavone-CH$_2$—Br, β-Naphthoflavone-CH$_2$—OH, Bestatin-amido-Me, MV-1-NH-Me, (S,S,S)-AHPC hydrochloride, and cIAP1 ligand 2.

In some embodiments of the disclosed PROTACs, $M_{E3}$ has a formula selected from:

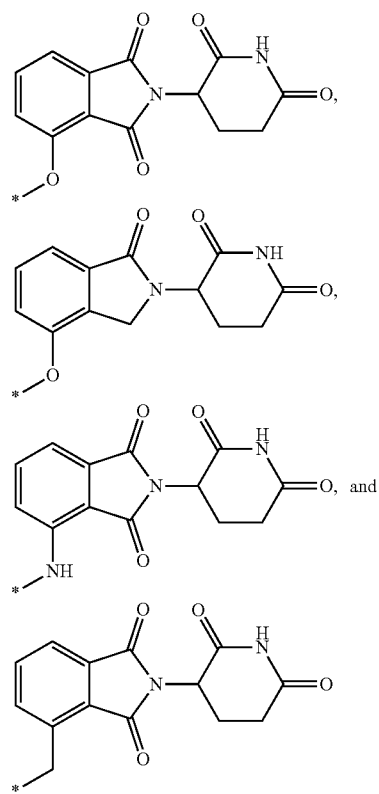

In some embodiments of the disclosed PROTACs, $M_{E3}$ has a formula selected from:

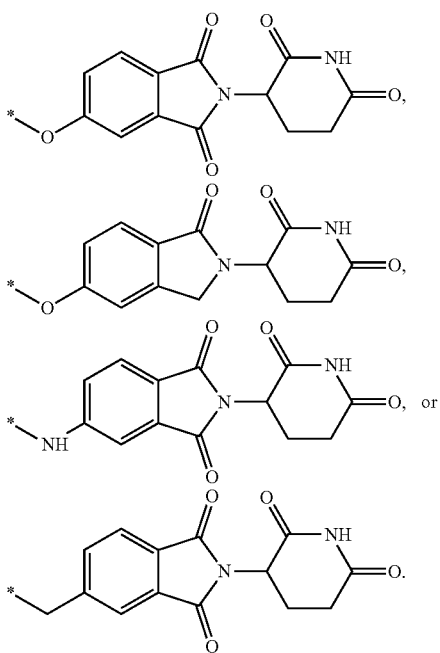

In some embodiments of the disclosed PROTACs, $M_{E3}$ has a formula:

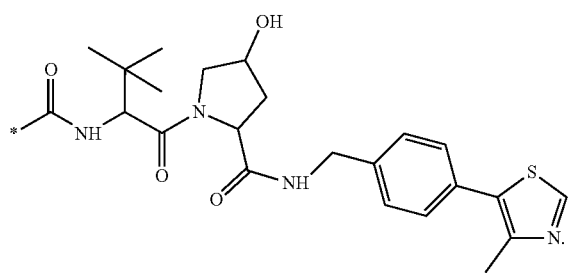 [SMILES: *C(=O)NC(C(=O)N1CC(O)CC1C(=O)NCc1ccc(-c2scnc2C)cc1)C(C)(C)C]

The disclosed compounds and PROTAC derived therefrom may be formulated as pharmaceutical compositions. In some embodiments, pharmaceutical compositions as contemplated herein include a compound or PROTAC as disclosed herein, for example, in an effective amount for treating a disease or disorder associated with EED, and a suitable pharmaceutical carrier, excipient, or diluent.

The disclosed compounds, PROTACs, and/or pharmaceutical compositions comprising the disclosed compound or PROTACs may be administered to subjects in need thereof, for example, to treat and/or prevent a disease or disorder associated with expression of EED. Suitable diseases or disorders associated with expression of EED may include cell proliferative diseases or disorders such as cancer. Suitable cancers treated and/or prevented in the disclosed methods may include, but are not limited to, multiple myeloma, leukemia, non-small cell lung cancer, colon cancer, cancer of the central nervous system, melanoma, ovarian cancer, renal cancer, prostate cancer, and breast cancer.

Use of the Disclosed Compounds and Proteolysis-Targeted Chimeric Molecules (PROTACs) for Inhibiting EED Activity The disclosed compounds and proteolysis-targeted chimeric molecules (PROTACs) may exhibit one or more biological activities. The disclosed compounds and PROTACs may inhibit the growth of cells that express EED (preferably by at least 50%, 60%, 70%, 80%, 90%, 95%, 96%, 97%, 98%, or 99% at a concentration of less than about 100 µM, 50 µM, 10 µM, 1 µM, 0.1 µM, 0.05 µM, 0.01 µM, 0.005 µM, 0.001 µM, or less). The disclosed compound and PROTACs may not inhibit the growth of cells that do not express EED (preferably by not more than 50%, 40%, 30%, 20%, 10%, 5%, 4%, 3%, 2% or less at a concentration of greater than about 0.001 µM, 0.005 µM, 0.01 µM, 0.5 µM, 0.1 µM, 1.0 µM, 10 µM, and 100 µM or higher). Concentration ranges also are contemplated herein, for example, a concentration range bounded by end-point concentrations selected from 0.001 µM, 0.005 µM, 0.01 µM, 0.5 µM, 0.1 µM, 1.0 µM, 10 µM, and 100 µM.

The disclosed compounds and PROTACs may be effective in inhibiting cell proliferation of cancer cells, including cancer cells that express EED and whose proliferation is inhibiting by inhibiting the biological activity of EED. The disclosed compounds and PROTACs may be effective in inhibiting cell proliferation of one or more types of cancer cells including: multiple myeloma cells, such as MM.1S cells; leukemia cells, such as CCRF-CEM, HL-60(TB), MOLT-4, RPMI-8226 and SR; non-small lung cancer cells, such as A549/ATCC, EKVX, HOP-62, HOP-92, NCI-H226, NCI-H23, NCI-H322M, NCI-H460 and NCI-H522; colon cancer cells, such as COLO 205, HCC-2998, HCT-116, HCT-15, HT29, KM12 and SW-620; CNS: SF-268, SF-295, SF-539, SNB-19, SNB-75 and U251; melanoma cancer cells, such as LOX IMVI, MALME-3M, M14, MDA-MB-435, SK-MEL-2, SK-MEL-28, SK-MEL-5, UACC-257 and UACC-62; ovarian cancer cells, such as IGR-OV1, OVCAR-3, OVCAR-4, OVCAR-5, OVCAR-8, NCI/ADR-RES and SK-OV-3; renal cancer cells, such as 786-0, A498, ACHN, CAKI-1, RXF 393, SN12C, TK-10 and UO-31; prostate cancer cells, such as DU-145 and PC-3; and breast cancer cells, such as MCF7, MDA-MB-231/ATCC, MDA-MB-468, HS 578T, BT-549 and T-47D.

Cell proliferation and inhibition thereof by the presently disclosed compounds and PROTACs may be assessed by cell viability methods disclosed in the art including colorimetric assays that utilize dyes such as MTT, XTT, and MTS to assess cell viability. Preferably, the disclosed compound and PROTACs have an $IC_{50}$ of less than about 10 µM, 5 µM, 1 µM, 0.5 µM, 0.01 µM, 0.005 µM, 0.001 µM or lower in the selected assay.

The disclosed compounds and PROTACs may be formulated as anti-cancer therapeutics, including hematologic malignancies, breast, lung, pancreas and prostate malignancies. The disclosed compounds and molecules also may be formulated as anti-inflammation therapeutics.

The disclosed compounds and PROTACs may be utilized in the methods disclosed herein may be formulated as pharmaceutical compositions that include: (a) a therapeutically effective amount of one or more compounds and molecules as disclosed herein; and (b) one or more pharmaceutically acceptable carriers, excipients, or diluents. The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to about 1000 mg/kg body weight (preferably about 0.5 to about 500 mg/kg body weight, more preferably about 50 to about 100 mg/kg body weight). In some embodiments, after the pharmaceutical composition is administered to a subject (e.g., after about 1, 2, 3, 4, 5, or 6 hours post-administration), the concentration of the compound at the site of action may be within a concentration range bounded by end-points selected from 0.001 µM, 0.005 µM, 0.01 µM, 0.5 µM, 0.1 µM, 1.0 µM, 10 µM, and 100 µM (e.g., 0.1 µM-1.0 µM).

The disclosed compounds and molecules and pharmaceutical compositions comprising the disclosed compounds and molecules may be administered in methods of treating a subject in need thereof. For example, in the methods of treatment a subject in need thereof may include a subject having a cell proliferative disease, disorder, or condition such as cancer (e.g., cancers such as multiple myeloma, leukemia, non-small cell lung cancer, colon cancer, cancer of the central nervous system, melanoma, ovarian cancer, renal cancer, prostate cancer, and breast cancer).

In some embodiments of the disclosed treatment methods, the subject may be administered a dose of a compound as low as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg once daily, twice daily, three times daily, four times daily, once weekly, twice weekly, or three times per week in order to treat the disease or disorder in the subject. In some embodiments, the subject may be administered a dose of a compound as high as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg, once daily, twice daily, three times daily, four times daily, once weekly, twice weekly, or three times per week in order to treat the disease or disorder in the subject. Minimal and/or maximal doses of the compounds and molecules may include doses falling within dose ranges having as end-points any of these disclosed doses (e.g., 2.5 mg-200 mg).

In some embodiments, a minimal dose level of a compound for achieving therapy in the disclosed methods of treatment may be at least about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000,15000, or 20000 ng/kg body weight of the subject. In some embodiments, a maximal dose level of a compound for achieving therapy in the disclosed methods of treatment may not exceed about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. Minimal and/or maximal dose levels of the compounds and molecules for achieving therapy in the disclosed methods of treatment may include dose levels falling within ranges having as end-points any of these disclosed dose levels (e.g., 500-2000 ng/kg body weight of the subject).

The compounds and molecules utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compounds and molecules utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds and molecules utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™). Suitable lubricants, including agents that act on the flowability of the powder to be compressed, may include colloidal silicon dioxide, such as Aerosil®200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds and molecules such as phenol, or quaternary compounds and molecules such as benzalkonium chloride.

Suitable diluents may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The compounds and molecules utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules. In some embodiments, the compounds and molecules are formulated as a composition for administration orally (e.g., in a solvent such as 5% DMSO in oil such as vegetable oil).

The compounds and molecules utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Pharmaceutical compositions comprising the compounds and molecules may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams.

For applications to the eye or other external tissues, for example the mouth and skin, the pharmaceutical compositions are preferably applied as a topical ointment or cream. When formulated in an ointment, the compound may be employed with either a paraffinic or a water-miscible ointment base. Alternatively, the compound may be formulated in a cream with an oil-in-water cream base or a water-in-oil base. Pharmaceutical compositions adapted for topical administration to the eye include eye drops where the active ingredient is dissolved or suspended in a suitable carrier, especially an aqueous solvent.

Pharmaceutical compositions adapted for nasal administration where the carrier is a solid include a coarse powder having a particle size (e.g., in the range 20 to 500 microns) which is administered in the manner in which snuff is taken (i.e., by rapid inhalation through the nasal passage from a container of the powder held close up to the nose). Suitable formulations where the carrier is a liquid, for administration as a nasal spray or as nasal drops, include aqueous or oil solutions of the active ingredient.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use.

Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

Combination Therapies and Pharmaceutical Compositions

The disclosed compounds and PROTACS or pharmaceutical compositions comprising the disclosed compounds and PROTACS may be administered in methods of treatment. For example, the disclosed compounds and PROTACS or pharmaceutical compositions comprising the disclosed compounds and PROTACS may be administered in methods of treating cell proliferative diseases and disorders. Cell proliferative diseases and disorders treated by the disclosed methods may include, but are not limited to, cancers selected from the group consisting of multiple myeloma, leukemia, non-small cell lung cancer, colon cancer, cancer of the central nervous system, melanoma, ovarian cancer, renal cancer, prostate cancer, and breast cancer.

Optionally, the disclosed compounds and PROTACS or pharmaceutical compositions comprising the disclosed compounds and PROTACS may be administered with additional therapeutic agents, optionally in combination, in order to treat cell proliferative diseases and disorders. In some embodiments of the disclosed methods, one or more additional therapeutic agents are administered with the disclosed compounds and PROTACS or with pharmaceutical compositions comprising the disclosed compounds and molecules, where the additional therapeutic agent is administered prior to, concurrently with, or after administering the disclosed compounds and PROTACS or the pharmaceutical compositions comprising the disclosed compounds and PROTACS. In some embodiments, the disclosed pharmaceutical composition are formulated to comprise the disclosed compounds and PROTACS and further to comprise one or more additional therapeutic agents, for example, one or more additional therapeutic agents for treating cell proliferative diseases and disorders.

ILLUSTRATIVE EMBODIMENTS

The following Embodiments are illustrative and should not be interpreted to limit the scope of the claimed subject matter.

Embodiment 1. A compound of a Formula I or a salt, hydrate, or solvate thereof:

I wherein
R$^1$ is hydrogen or R$^1$ has a formula:

*—(Ph)$_n$—(N⌒N)$_x$—R$^2$, wherein
Ph is phenyl;
n is 0 or 1;
x is 0 or 1; and
R$^2$ is hydrogen, alkyl, alkoxy, —C(O)—H, —C(O)—(CH$_2$)$_m$—CH$_3$ where m is 0-20, —C(O)—(CH$_2$CH$_2$O)$_n$—H or —C(O)—(CH$_2$CH$_2$O)$_n$—CH$_3$ where m is 1-20, —C(O)—CH$_2$OCH$_3$, —C(O)—CH$_2$—CH(CH$_2$CH$_2$CH$_3$)$_2$, —S(O)(O)—H, or —S(O)(O)—CH$_3$.

Embodiment 2. The compound of embodiment 1, wherein R$^1$ is selected from:

Embodiment 3. The compound of embodiment 1, wherein R$^1$ is selected from:

(CH$_2$)$_m$CH$_3$ where m is 0-20, and (CH$_2$CH$_2$O)$_m$CH$_3$ where m is 0-20.

Embodiment 4: The compound of embodiment 1 selected from N-(furan-2-ylmethyl)-8-(4-(piperazin-1-yl)phenyl)-[1,2,4]triazolo[4,3-c]pyrimidin-5-amine (8), NUCC-0226131, NUCC-0226130, NUCC-0226129, NUCC-0226128, NUCC-0226127, NUCC-0226126, NUCC-0226126, NUCC-0226124, NUCC-0226124, NUCC-0226122, NUCC-0226121, NUCC-0226120, and NUCC-0226120.

Embodiment 5. A molecule having a formula: M$_{EED}$-L-M$_{E3}$ or a salt, hydrate, or solvate thereof, wherein M$_{EED}$ is a moiety that binds to EED, L is a bond or a linker covalently attaching M$_{EED}$ and M$_{E3}$, and M$_{E3}$ is a moiety that binds to an E3 ubiquitin ligase.

Embodiment 6. The molecule of embodiment 5, wherein M$_{EED}$ has a Formula II

II wherein
Ph is phenyl;
n is 0 or 1;
x is 0 or 1; and
R$^2$ is a bond or carbonyl.

Embodiment 7. The molecule of embodiment 5 or 6, wherein M$_{EED}$ has a formula selected from:

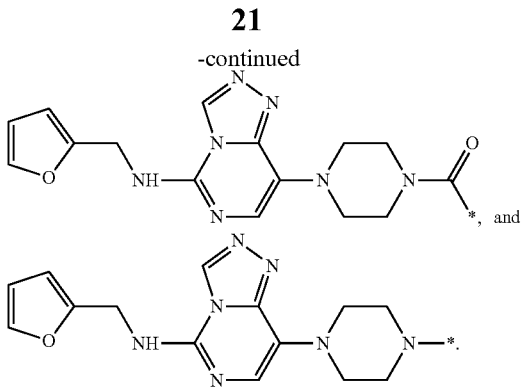

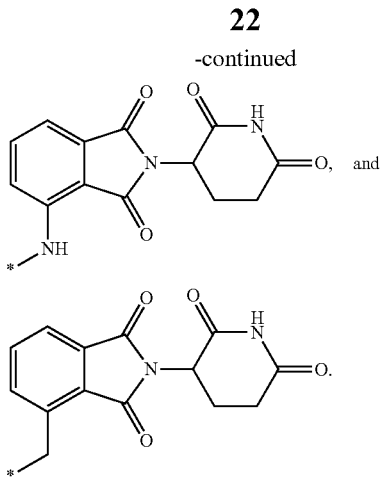

Embodiment 8. The molecule of any of embodiments 5-7, wherein L comprises a polyethylene glycol moiety, an alkylalkyne moiety, and/or an aminoalkyl alkyne moiety.

Embodiment 9. The molecule of any of embodiments 5-8, wherein L has a formula selected from: —(CH$_2$)$_m$—, —(CH$_2$)$_m$CH$_2$CH$_2$C(O)NHCH$_2$CH$_2$—, —(CH$_2$)$_m$CH$_2$CH$_2$C(O)NHCH$_2$CH$_2$CH$_2$—, —(CH$_2$CH$_2$O)$_n$CH$_2$CH$_2$C(O)NHCH$_2$CH$_2$—, —(CH$_2$CH$_2$O)$_n$CH$_2$CH$_2$C(O)NHCH$_2$CH$_2$CH$_2$—, —(CH$_2$CH$_2$O)$_n$CH$_2$CH$_2$—, —(CH$_2$CH$_2$O)$_n$CH$_2$—, —(CH$_2$)$_m$C(O)NHCH$_2$CH$_2$—, —(CH$_2$CH$_2$O)$_n$CH$_2$CH$_2$C(O)NHCH$_2$CH$_2$—, —CH$_2$CH$_2$C(O)NHCH$_2$CH$_2$CH$_2$—, —CH$_2$CH$_2$C(O)NHCH$_2$CH$_2$CH$_2$C(O)NHCH$_2$CH$_2$, —CH$_2$CH$_2$C(O)NHCH$_2$CH$_2$CH$_2$C(O)NHCH$_2$CH$_2$C(O)NHCH$_2$CH$_2$, —CH$_2$CH$_2$C(O)NHCH$_2$CH$_2$CH$_2$C(O)NHCH$_2$CH$_2$CH$_2$, —(CH$_2$CH$_2$O)$_n$CH$_2$CH$_2$—, —CH$_2$O(CH$_2$)$_m$—, —CH$_2$OCH$_2$C(O)NHCH$_2$CH$_2$—, —CH$_2$OCH$_2$C(O)NHCH$_2$CH$_2$CH$_2$—, and —CH$_2$OCH$_2$C(O)NHCH$_2$CH$_2$C(O)NHCH$_2$CH$_2$—, —CH$_2$OCH$_2$C(O)NHCH$_2$CH$_2$CH$_2$C(O)NHCH$_2$CH$_2$CH$_2$—, wherein m and n are 0-20.

Embodiment 10. The molecule of any of embodiments 5-9, wherein M$_{E3}$ is a moiety that binds to an E3 ubiquitin ligase selected from Von Hippel-Lindau (VHL) E3 ubiquitin ligase, cereblon (CRBN) E3 ubiquitin ligase, inhibitor of apoptosis protein (IAP) E3 ubiquitin ligase, and mouse double minute 2 homolog (MDM2) E3 ubiquitin ligase.

Embodiment 11. The molecule of any of embodiments 5-10, wherein M$_{E3}$ comprises a thalidomide moiety, a pomalidomide moiety, a lenalidomide moiety, VHL ligand 1 (VHL-1), VHL ligand 2 (VHL-2), VH032, VL-269, LCL161, hydroxyproline-based ligands, or HIF-1α-derived (R)-hydroxyproline.

Embodiment 12. The molecule of any of embodiments 5-11, wherein M$_{E3}$ has a formula selected from:

Embodiment 13. The molecule of any of embodiments 5-11, wherein M$_{E3}$ has a formula

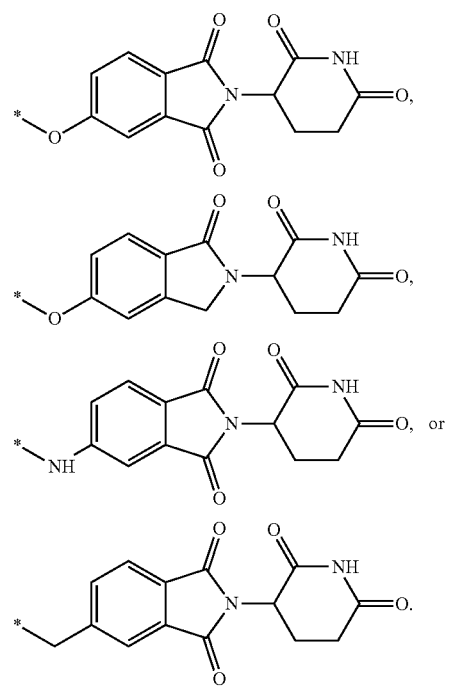

Embodiment 14. The molecule of any of embodiments 5-11, wherein M$_{E3}$ has a formula:

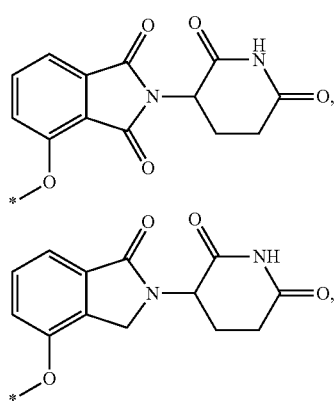

Embodiment 15. The molecule of claim 5 selected from NUCC-0223591, NUCC-0223590, NUCC-0223590, NUCC-0223588, NUCC-0223587, NUCC-0223586, NUCC-0223585, NUCC-0203228, NUCC-0203227, NUCC-0203226, NUCC-0203225, NUCC-0203224, NUCC-0203222, NUCC-0203221, NUCC-0203220, and NUCC-0203219.

Embodiment 16. A pharmaceutical composition comprising a compound of any of embodiments 1-4 or the molecule of any of embodiments 4-15 and a suitable pharmaceutical carrier, excipient, or diluent.

Embodiment 17. A method of treating cancer, the method comprising administering the composition of embodiment 16 to a subject having the cancer.

Embodiment 18. The method of embodiment 17, wherein the cancer is selected from multiple myeloma, leukemia, non-small cell lung cancer, colon cancer, cancer of the central nervous system, melanoma, ovarian cancer, renal cancer, prostate cancer, and breast cancer.

EXAMPLES

The following examples are illustrative and should not be interpreted to limit the scope of the claimed subject matter.

Example 1—Embryonic Ectoderm Development (EED) Protein Binding Compounds and Proteolysis-Targeting Chimeric (PROTAC) Derivatives Thereof The Table of Compounds shows representative compounds of the present disclosure. Exemplary methods for preparing the compounds are shown below.

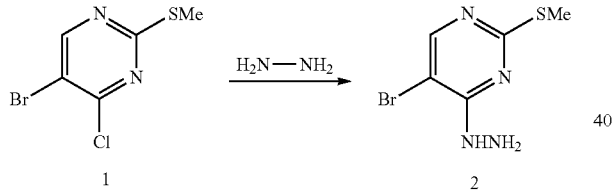

Synthesis of 5-bromo-4-hydrazineyl-2-(methylthio)pyrimidine (2). To a 40 mL vial was added a solution of 5-bromo-4-chloro-2-(methylthio)pyrimidine (1.500 g, 1 Eq, 6.263 mmol) in Ethanol (25 mL), followed by dropwise addition of hydrazine (402 mg, 0.394 mL, 2.00 Eq, 12.5 mmol). The reaction mixture was allowed to stir at room temperature overnight. LCMS (184-001-1) showed complete conversion. The resulting suspension was filtered, washed with hexanes and dried in vacuo to give the desired compound 5-bromo-4-hydrazineyl-2-(methylthio)pyrimidine (1.47 g, 6.25 mmol, 99.8%) as a white solid. LCMS (ESI) [M+H]⁺: 235.1.

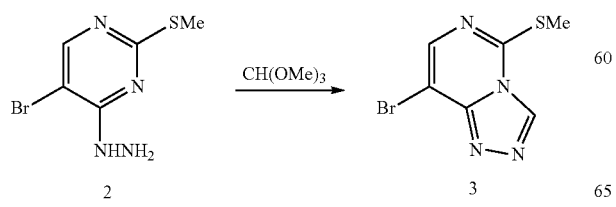

Synthesis of 8-bromo-5-(methylthio)-[1,2,4]triazolo[4,3-c]pyrimidine (3). To a microwave vial was added 5-bromo-4-hydrazineyl-2-(methylthio)pyrimidine (250 mg, 1 Eq, 1.06 mmol) in trimethyl orthoformate (1.3 mL) and allowed stir at 110° C. overnight. LCMS showed complete conversion and the resulting reaction mixture was allowed to cool down to room temperature and concentrated to dryness. The crude mixture was concentrated on silica and purified via flash chromatography with EtOAc:Hexane to give the title compound 8-bromo-5-(methylthio)-[1,2,4]triazolo[4,3-c]pyrimidine (135 mg, 551 μmol, 51.8%) as a white solid.

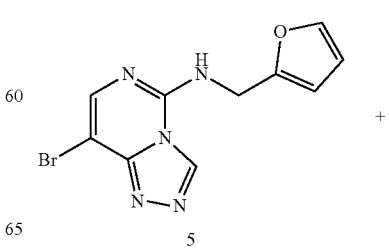

Synthesis of 8-bromo-N-(furan-2-ylmethyl)-[1,2,4]triazolo[4,3-c]pyrimidin-5-amine (5). To a 20 mL vial containing 8-bromo-5-(methylthio)-[1,2,4]triazolo[4,3-c]pyrimidine (500 mg, 1 Eq, 2.04 mmol) was added furan-2-ylmethanamine (6.93 g, 6.31 mL, 35 Eq, 71.4 mmol) and allowed to stir at room temperature overnight. The reaction was concentrated and purified by flash silico gel chromatography eluting with MeOH/DCM.

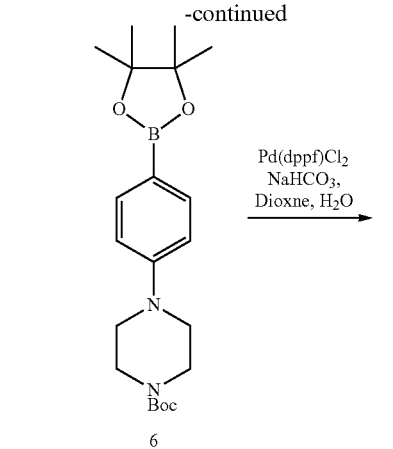

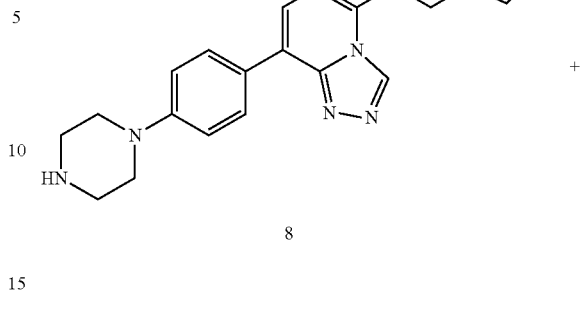

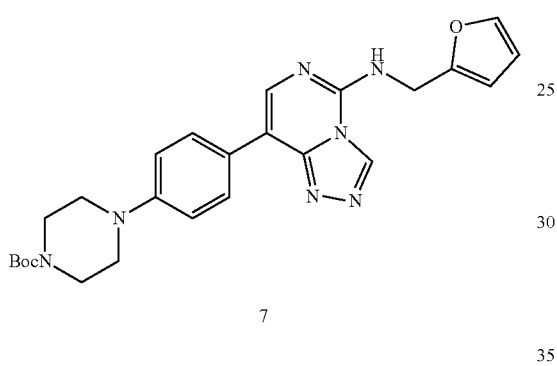

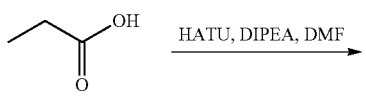

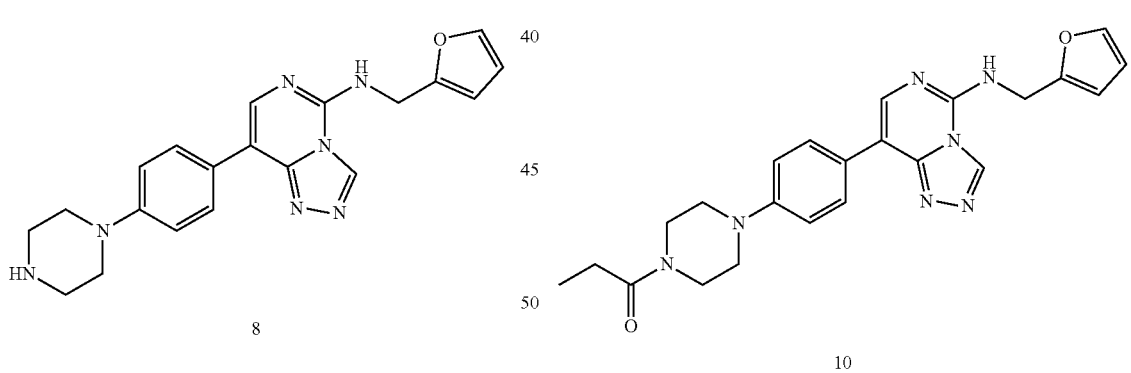

Synthesis of N-(furan-2-ylmethyl)-8-(4-(piperazin-1-yl)phenyl)-[1,2,4]triazolo[4,3-c]pyrimidin-5-amine (8). To a microwave vial was added 8-bromo-N-(furan-2-ylmethyl)-[1,2,4]triazolo[4,3-c]pyrimidin-5-amine (700 mg, 1 Eq, 2.38 mmol), tert-butyl 4-(4-(4,4,5,5-tetramethyl-1,3,2-dioxaborolan-2-yl)phenyl)piperazine-1-carboxylate (1.11 g, 1.2 Eq, 2.86 mmol), Pd(dppf)Cl2 (279 mg, 0.16 Eq, 381 μmol) and sodium bicarbonate (500 mg, 2.5 Eq, 5.95 mmol) in 1,4-Dioxane (6 mL) and Water (3 mL) and allowed to stir at 110° C. overnight. LCMS shows complete conversion. The mixture was purified by flash silica gel chromatography eluting with MeOH/DCM to afford the Boc-protected target compound (1.0 g, 90%). This material was then stirred with HCl/Dioxane for 2 hrs at rt and concentrated to afford the title compound (0.89 g, 99%).

Synthesis of 1-(4-(4-(5-((furan-2-ylmethyl)amino)-[1,2,4]triazolo[4,3-c]pyrimidin-8-yl)phenyl)piperazin-1-yl)propan-1-one (10). A solution containing N-(furan-2-ylmethyl)-8-(4-(piperazin-1-yl)phenyl)-[1,2,4]triazolo[4,3-c]pyrimidin-5-amine (60 mg, 0.16 mmol), HATU (73 mg, 1.2 Eq, 0.19 mmol), and DIPEA (0.17 mL, 6 Eq, 0.96 mmol) in DMF (1 mL) was stirred for 5 min before addition of propionic acid (18 μL, 1.5 Eq, 0.24 mmol). Upon completion, the reaction was diluted with acetonitrile and purified by prep-HPLC using 10-90% ACN with 0.1% formic acid to afford the title compound (18.3 mg, 27%).

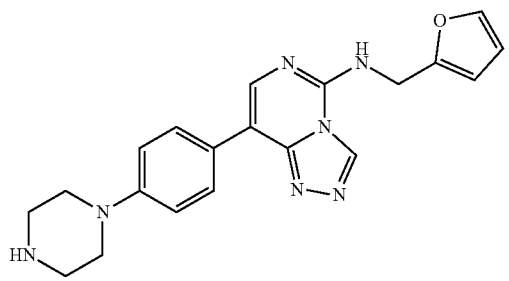

8

+

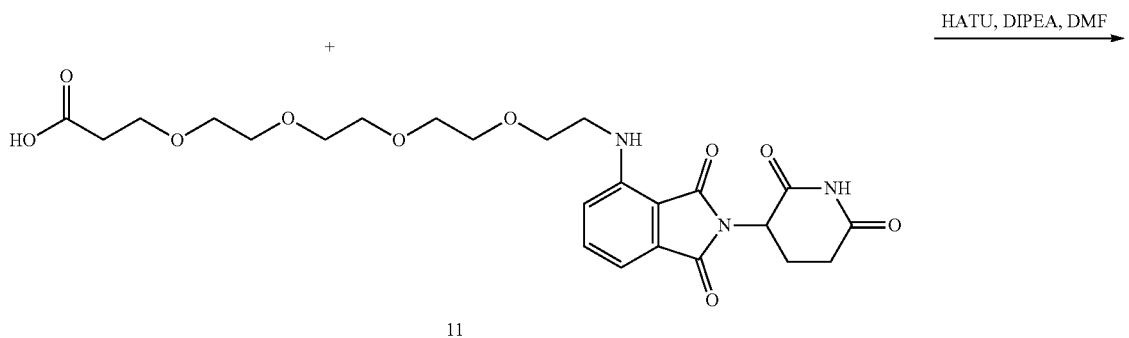

11

HATU, DIPEA, DMF

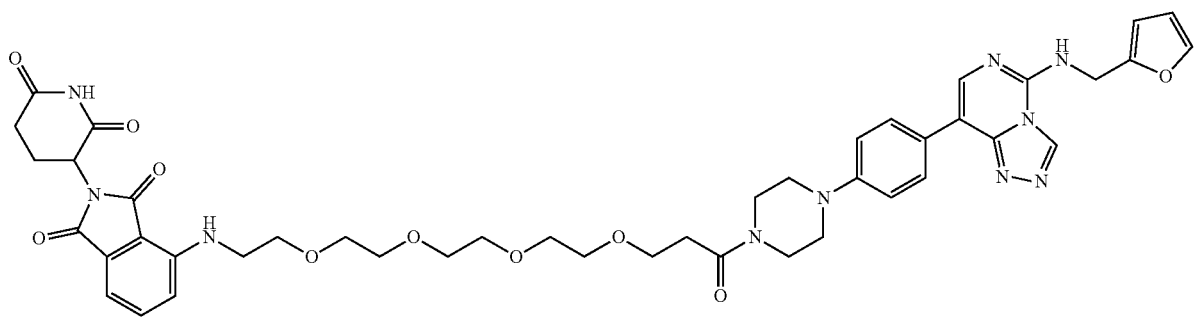

12
NUCC-0223591

Synthesis of 2-(2,6-dioxopiperidin-3-yl)-4-(16-{4-[4-(5-{[(furan-2-yl)methyl]amino}-[1,2,4]triazolo[4,3-c]pyrimidin-8-yl)phenyl]piperazin-1-yl}-16-oxo-4,7,10,13-tetraoxa-1-azahexadecan-1-yl)-2,3-dihydro-1H-isoindole-1,3-dione (12, NUCC-0223591). A solution containing N-(furan-2-ylmethyl)-8-(4-(piperazin-1-yl)phenyl)-[1,2,4]triazolo[4,3-c]pyrimidin-5-amine (18 mg, 48 μmol), HATU (18 mg, 1 Eq, 48 μmol), and DIPEA (25 μL, 3 Eq, 0.14 mmol) in DMF (1 mL) was stirred for 5 min before addition of 1-((2-(2,6-dioxopiperidin-3-yl)-1,3-dioxoisoindolin-4-yl)amino)-3,6,9,12-tetraoxapentadecan-15-oic acid (25 mg, 1 Eq, 48 umol). Upon completion, the reaction was diluted with acetonitrile and purified by prep-HPLC using 10-90% ACN with 0.1% formic acid to afford the title compound (13.5 mg, 32%).

Synthesis of Compounds:
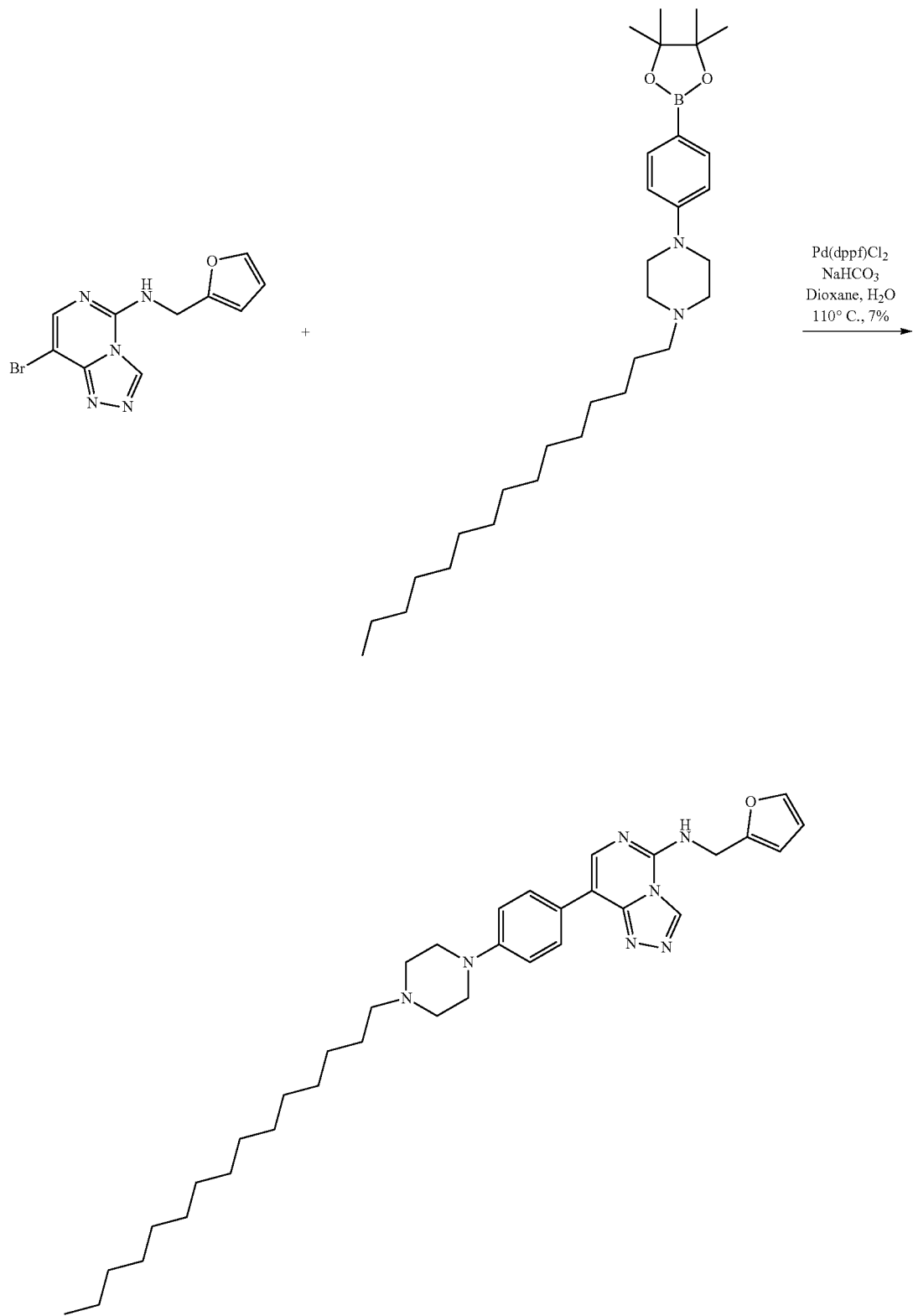

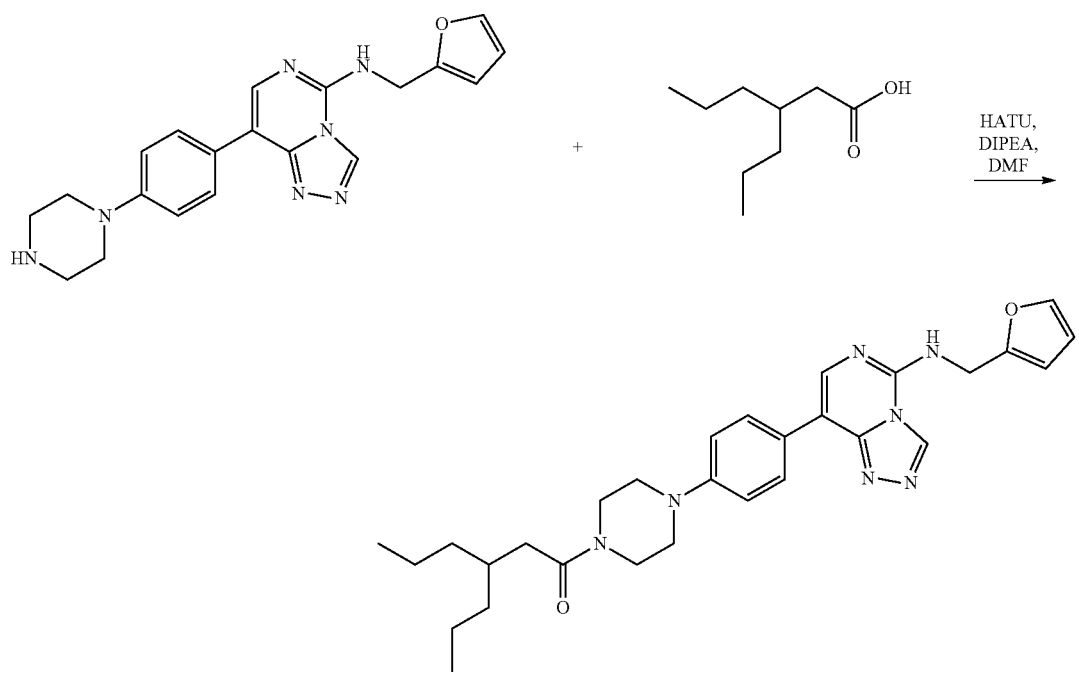
NUCC-0226131
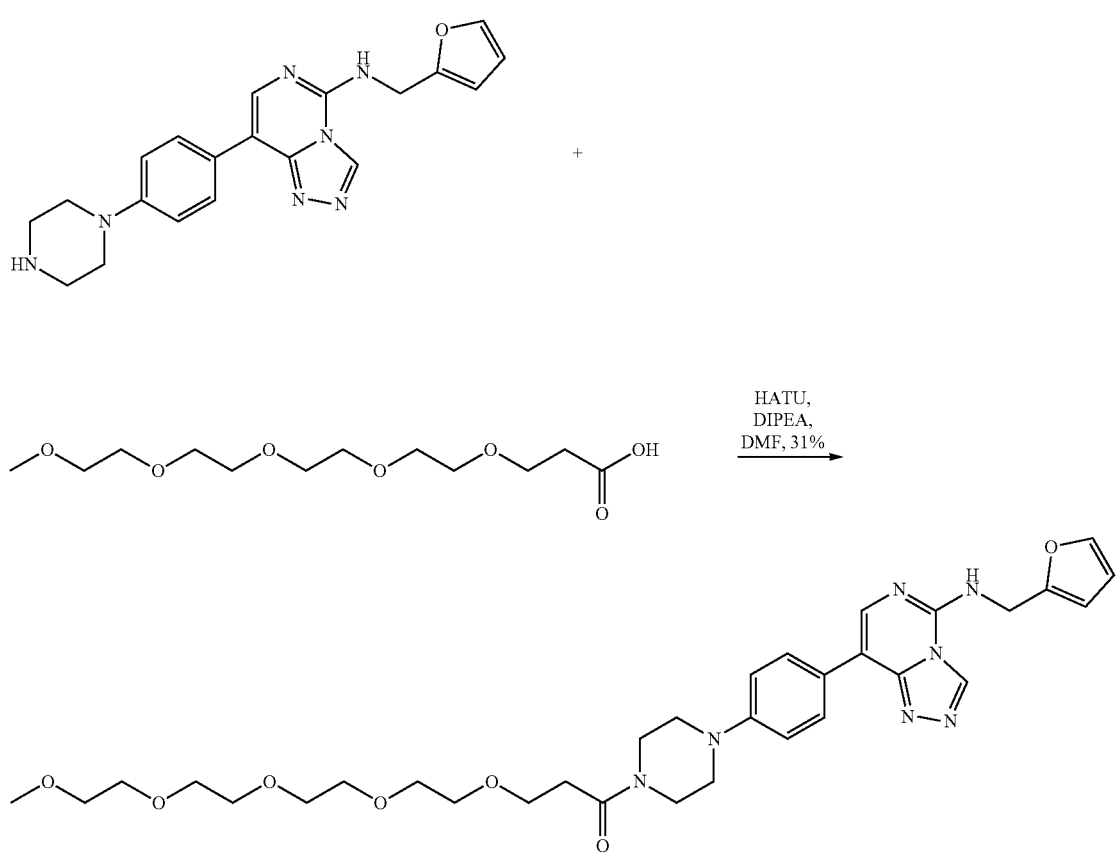
NUCC-0226130

-continued
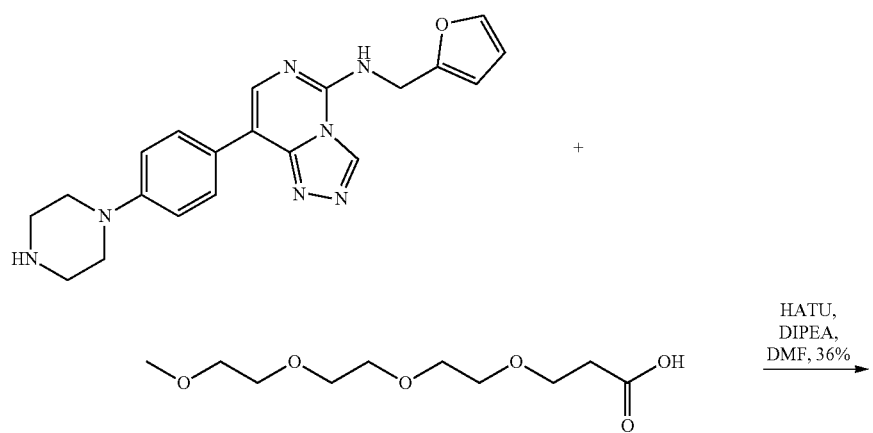
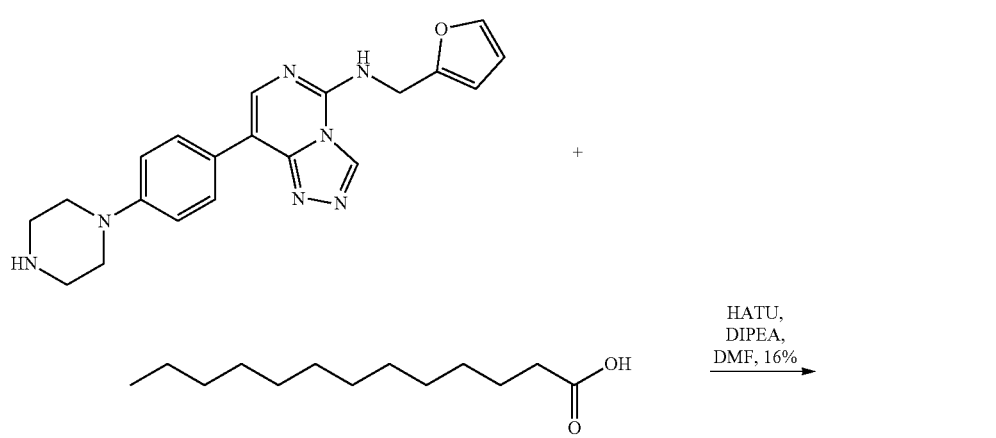

-continued
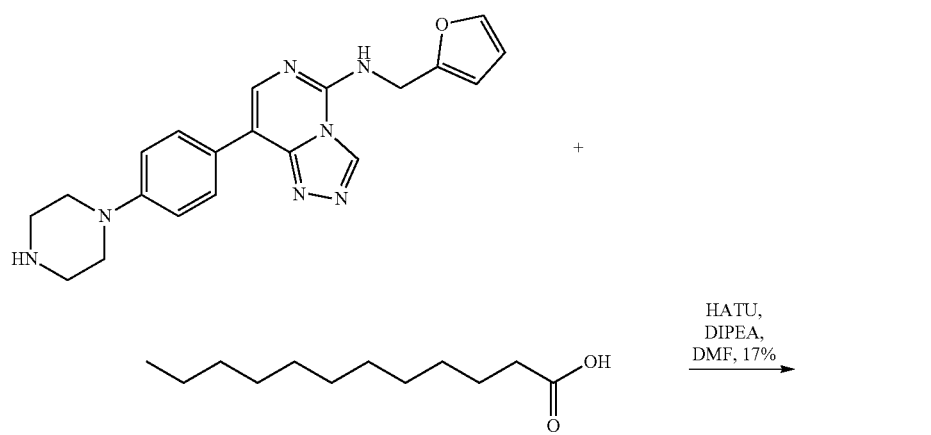
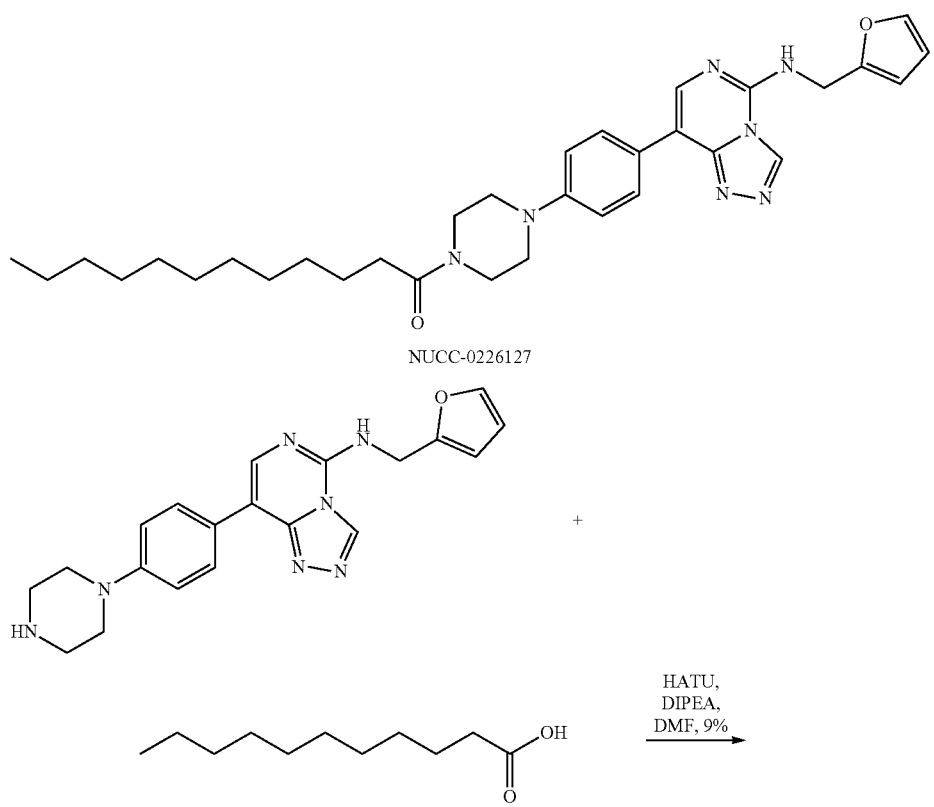
NUCC-0226127
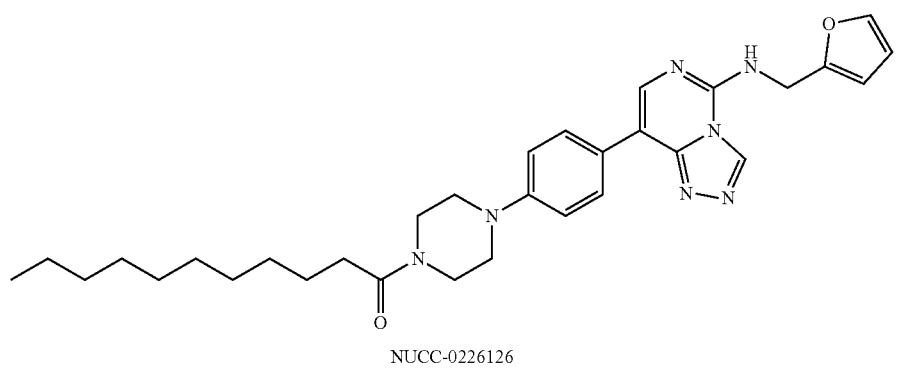
NUCC-0226126

-continued
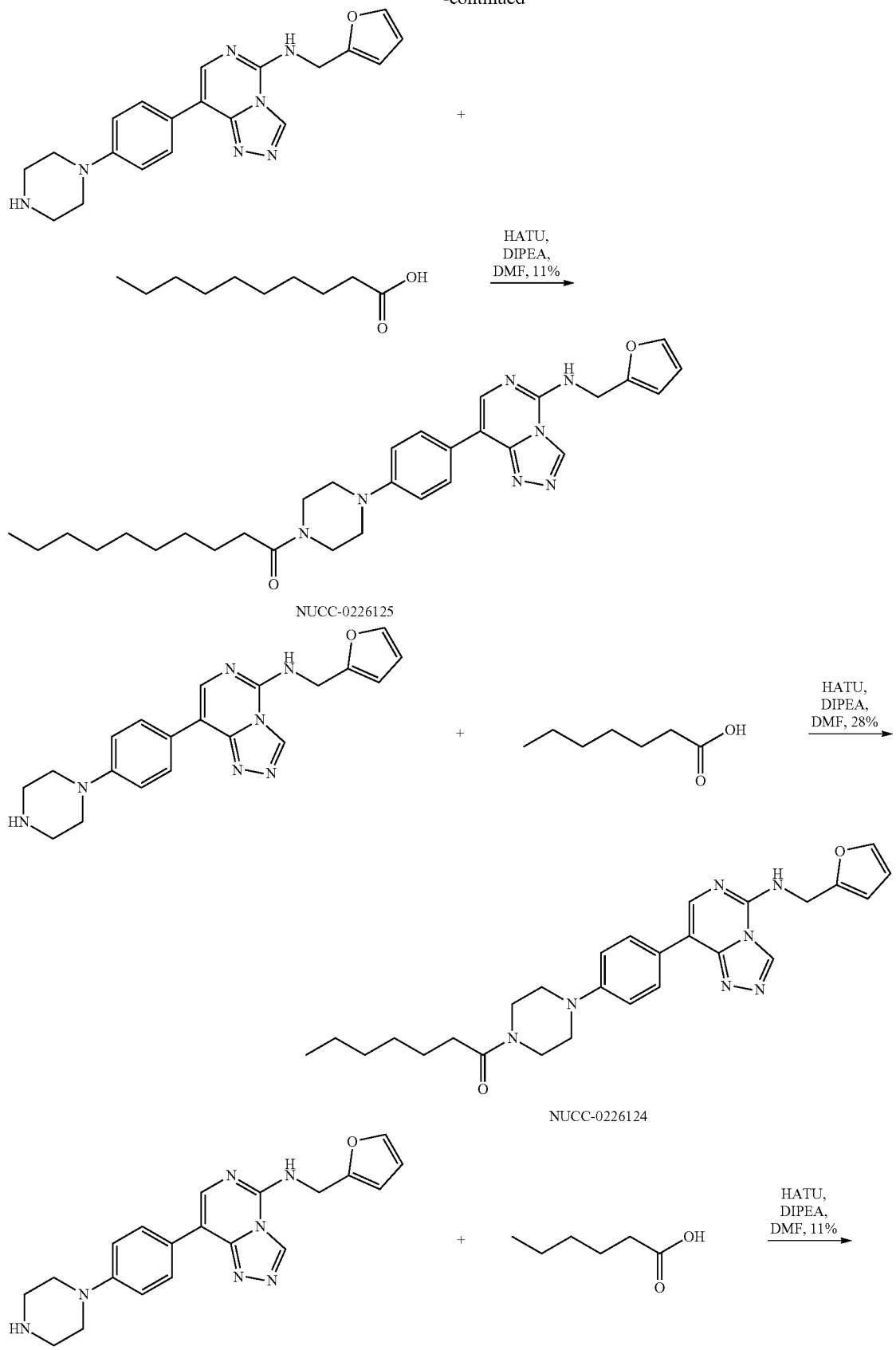

-continued
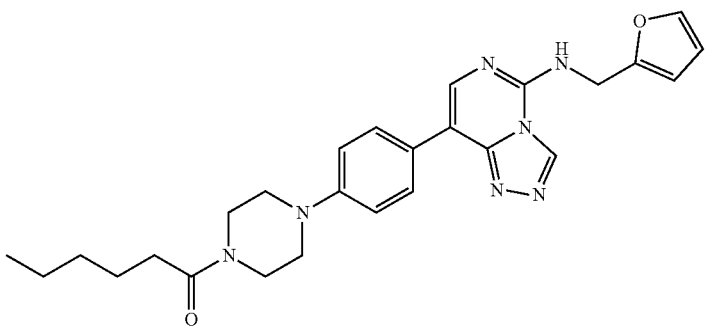
NUCC-0226123
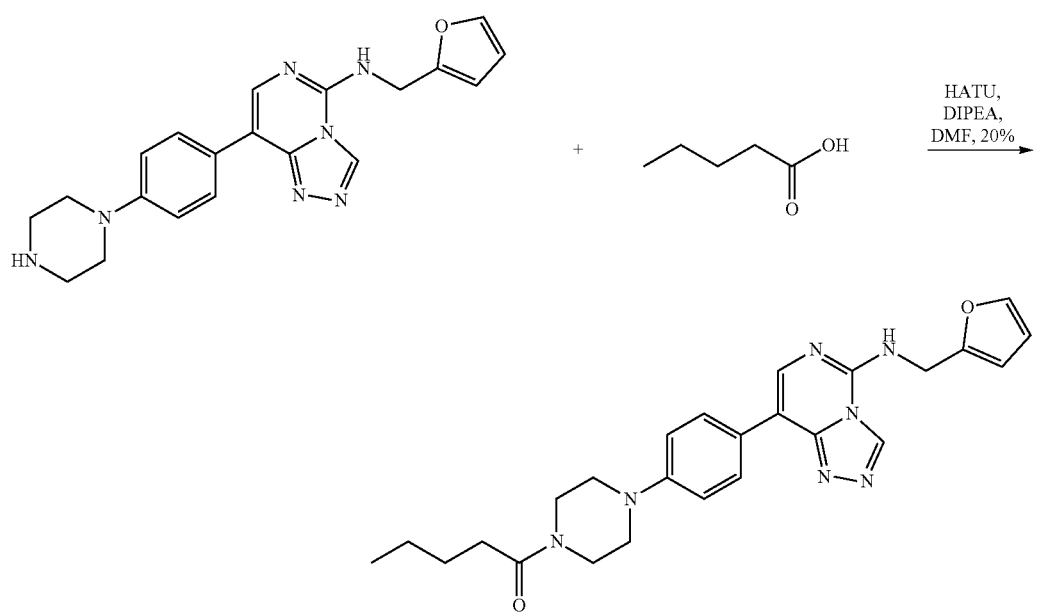
NUCC-0226122
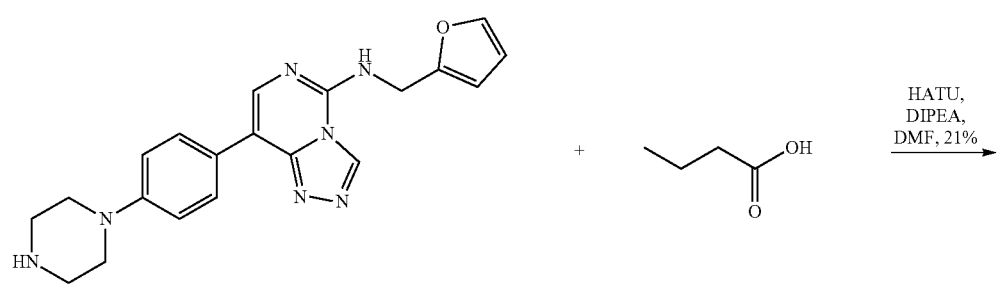
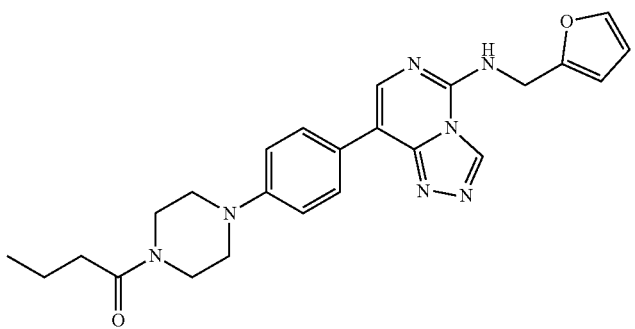
NUCC-0226121

-continued
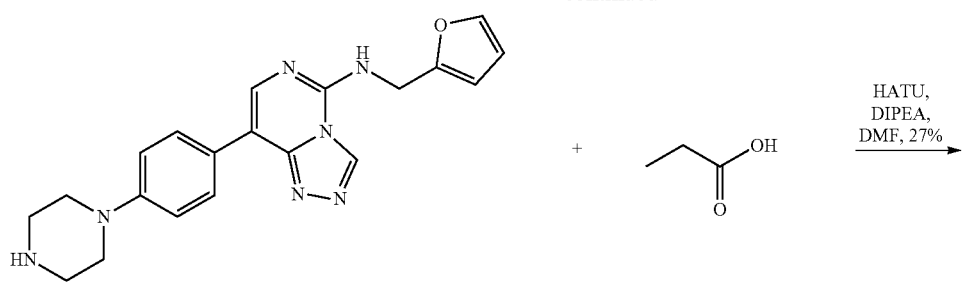
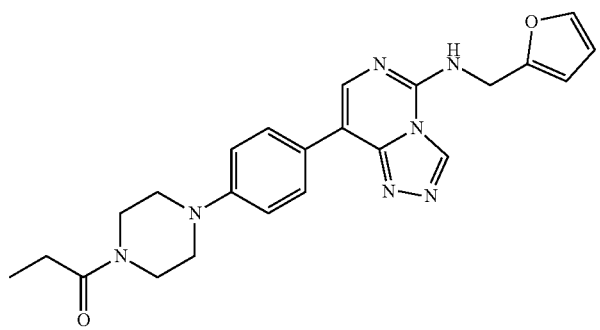
NUCC-0226120
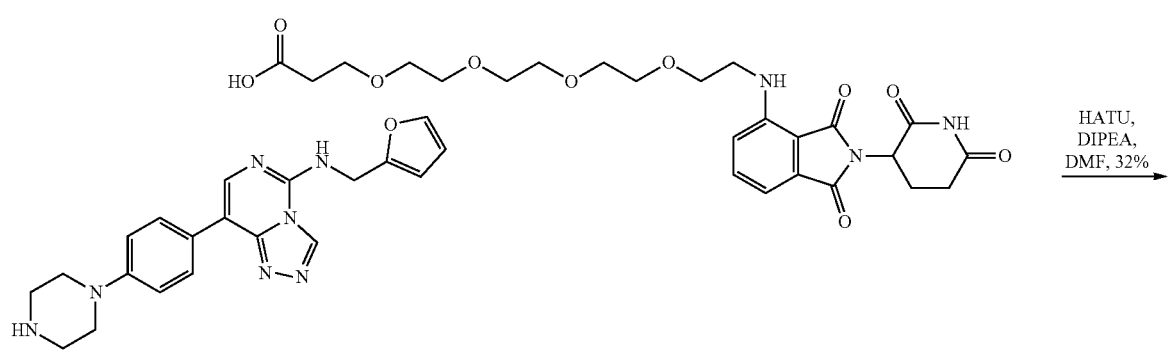
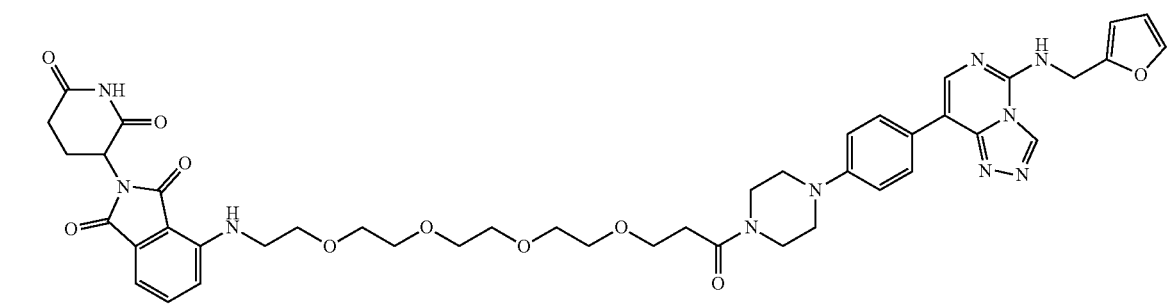
NUCC-0223591
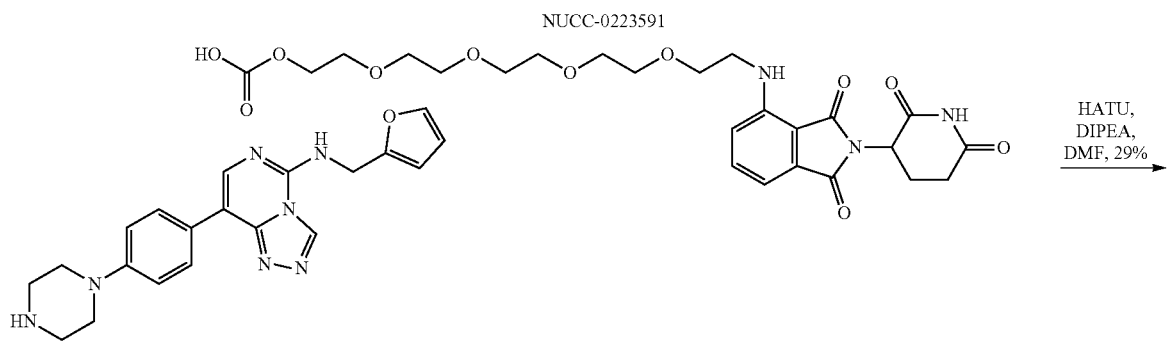

-continued
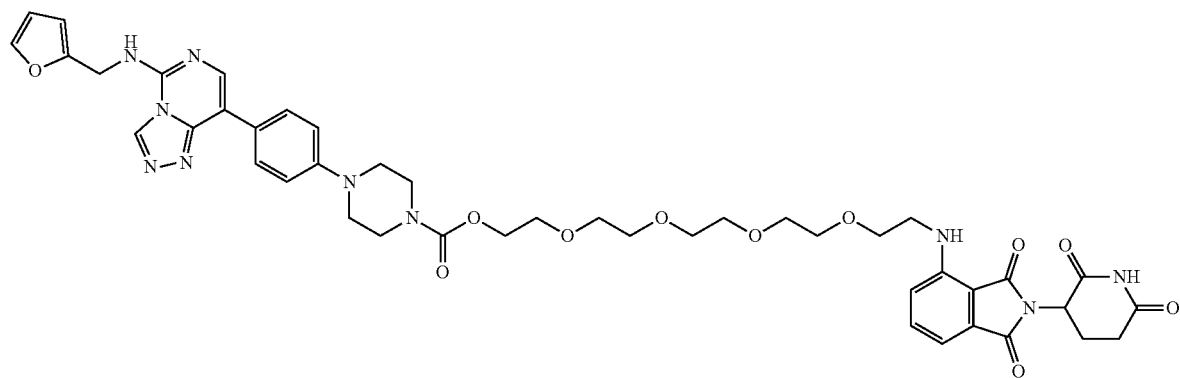
NUCC-0223590
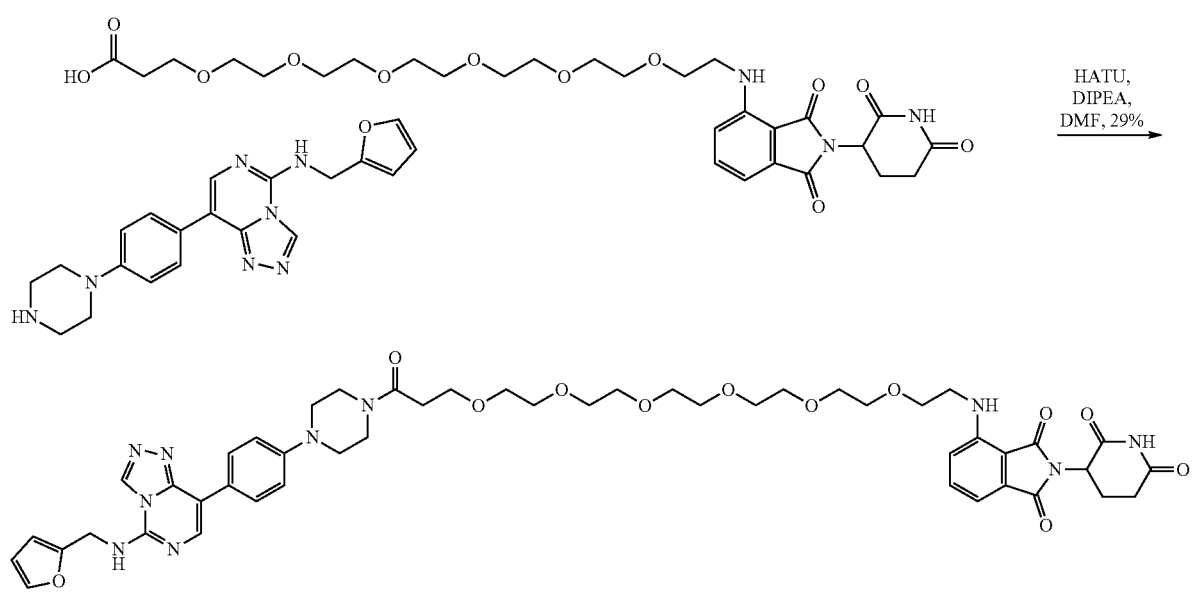
NUCC-0223589
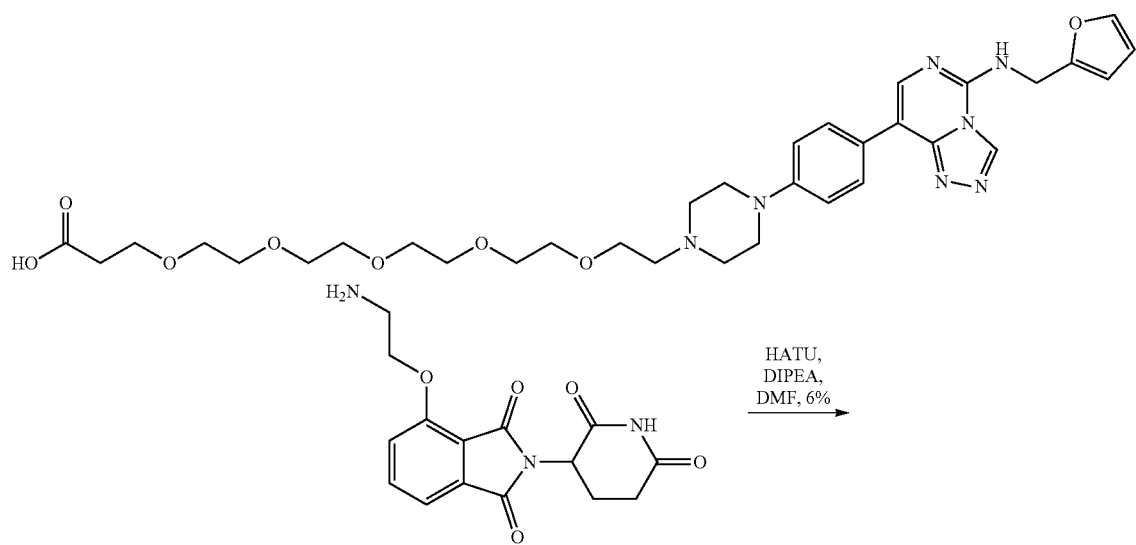

-continued
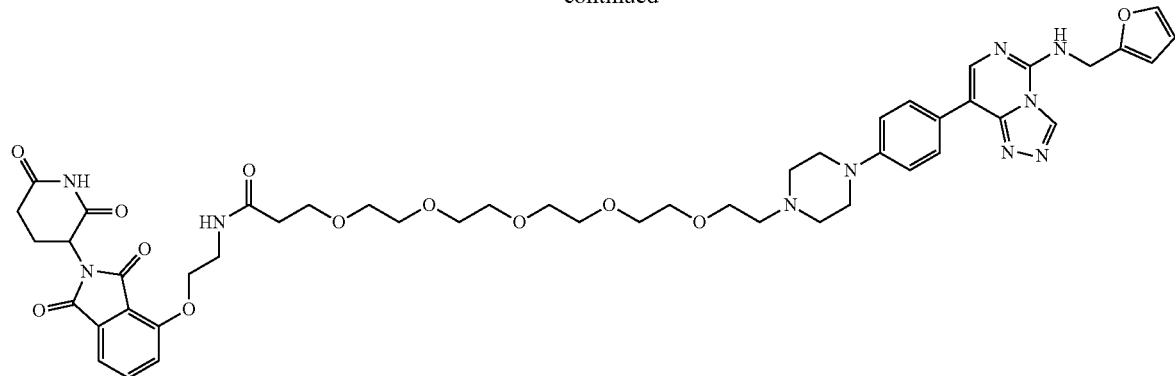
NUCC-0233588
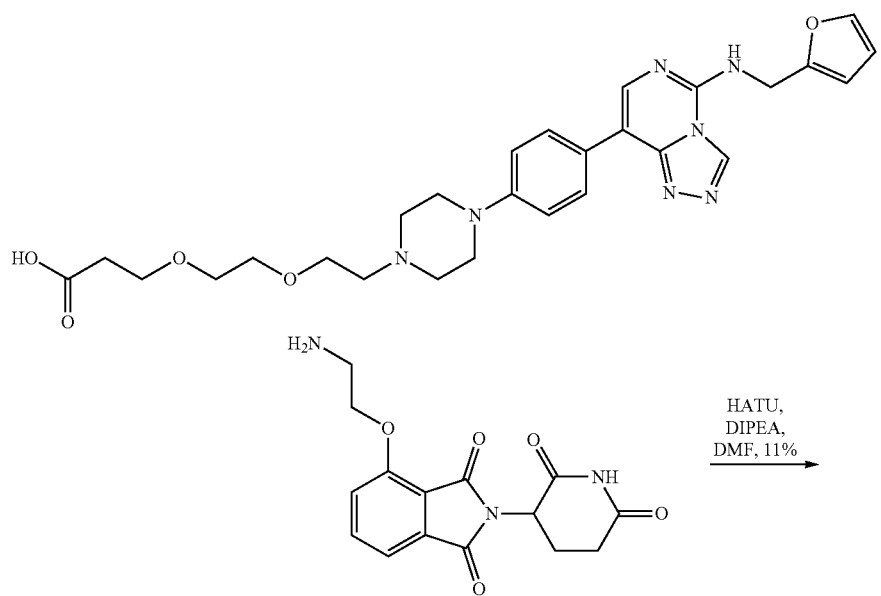
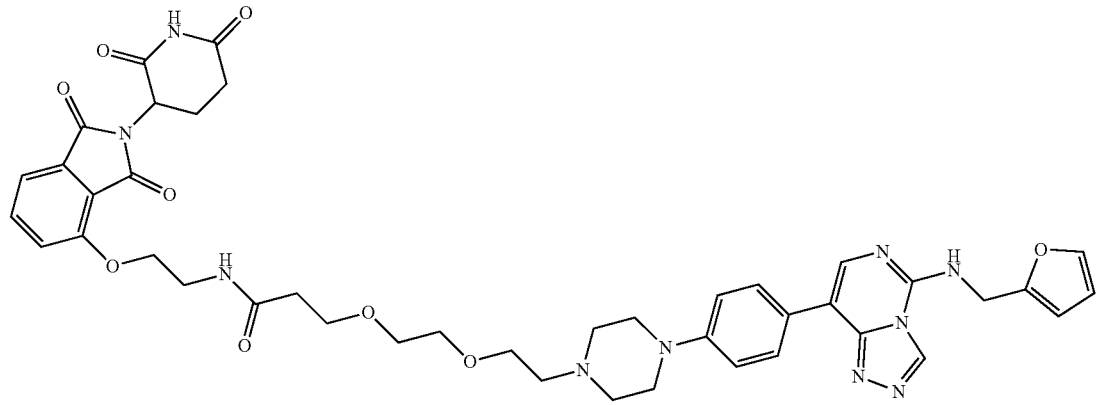
NUCC-0223587
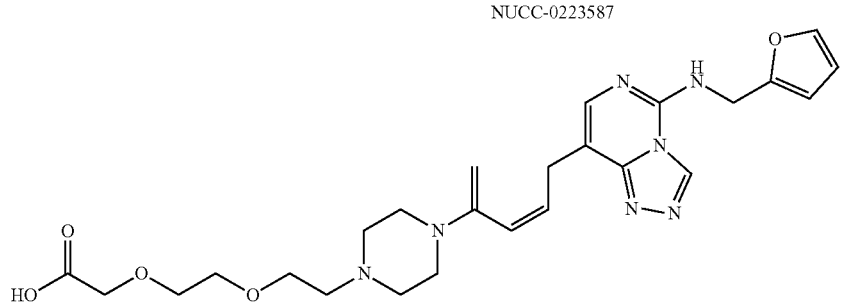

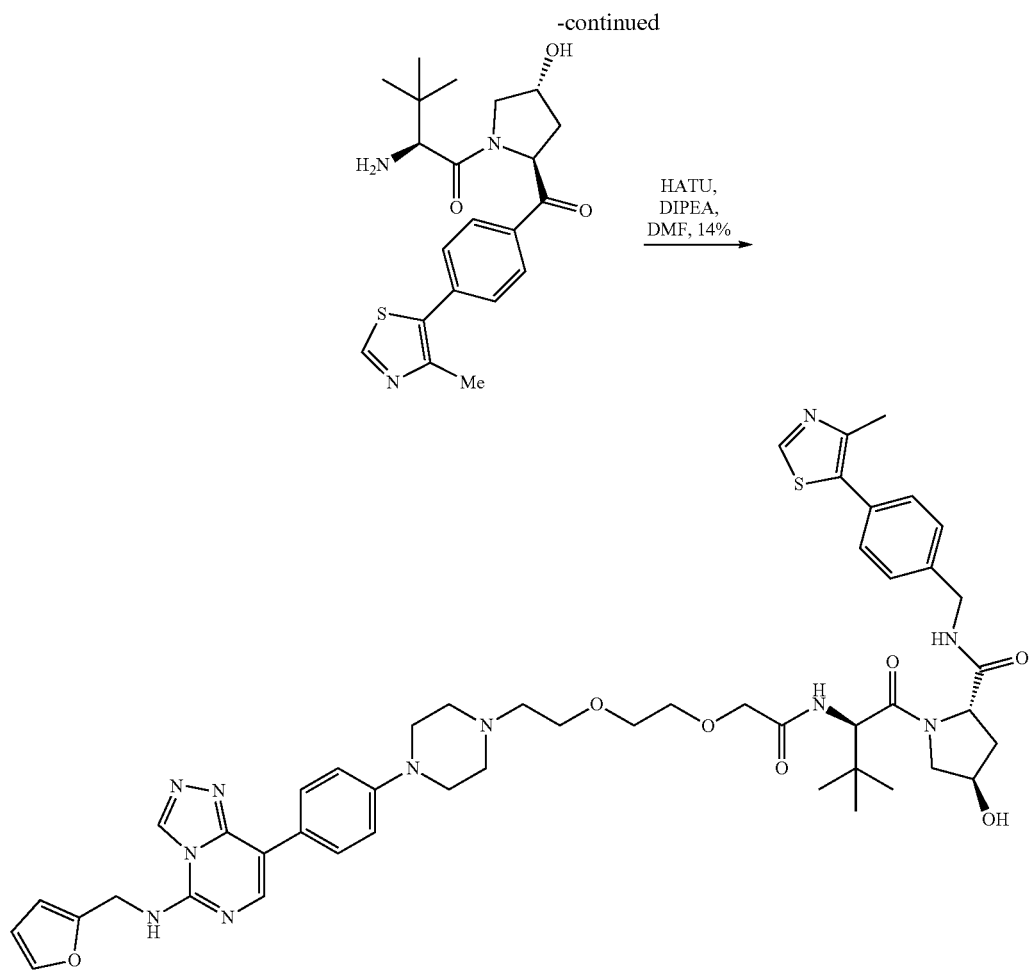
NUCC-0223586
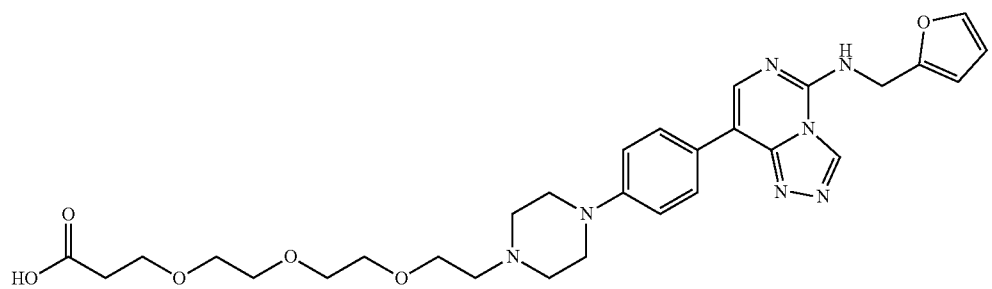
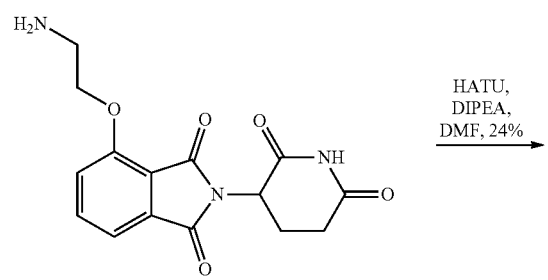

-continued
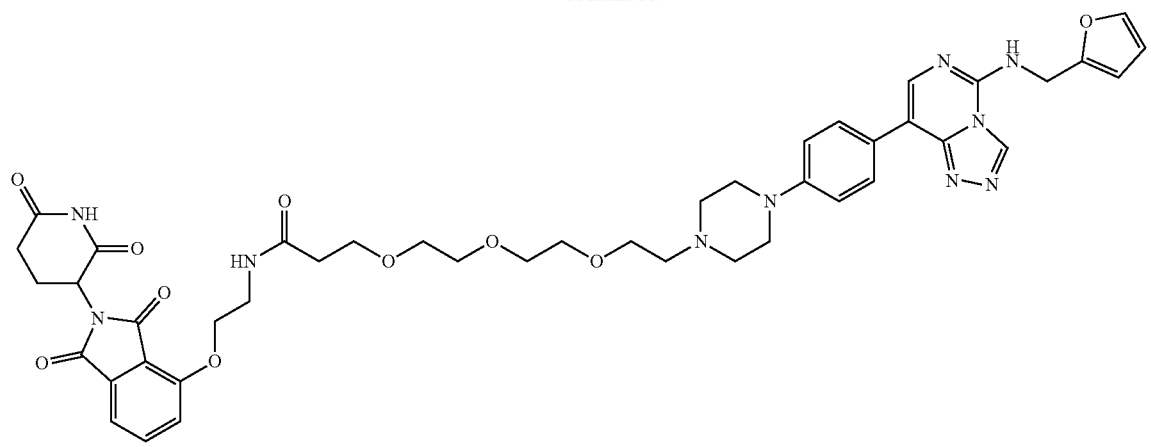
NUCC-0223585
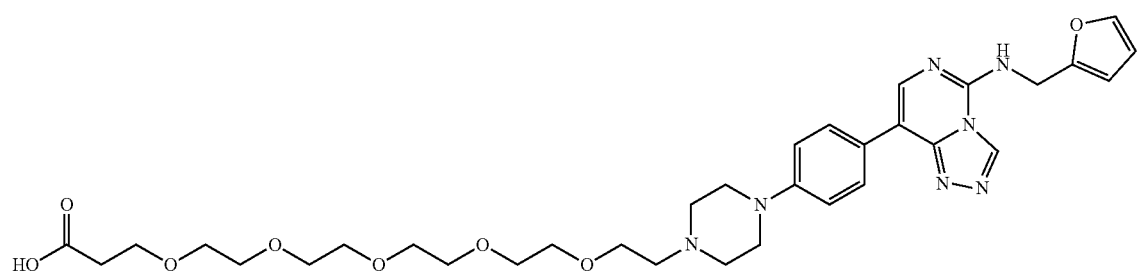
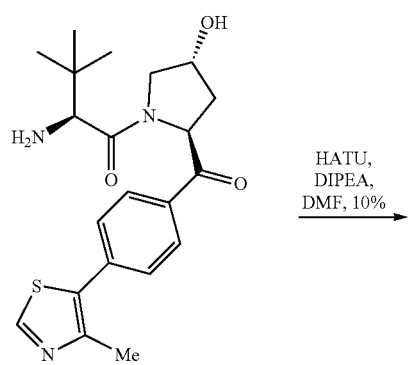
→ HATU, DIPEA, DMF, 10%

-continued
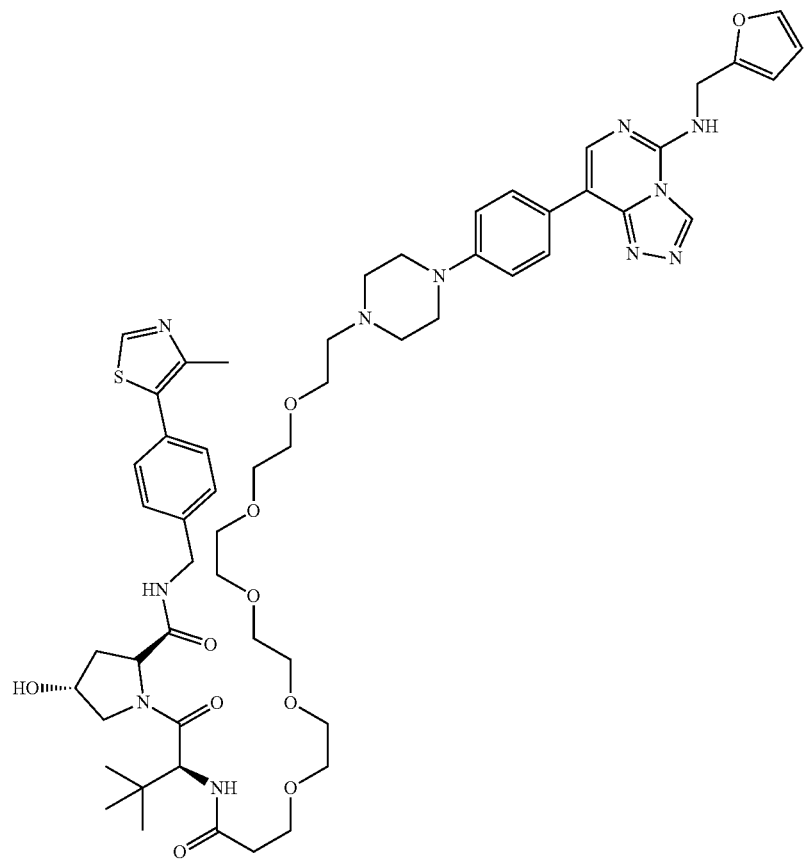
NUCC-0203228
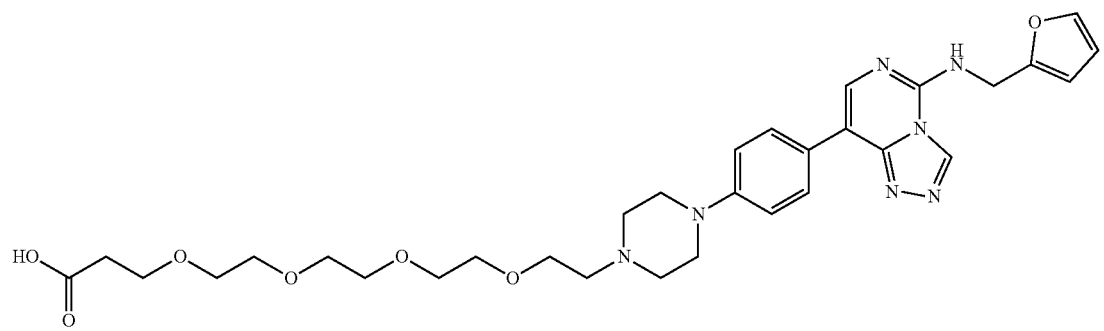
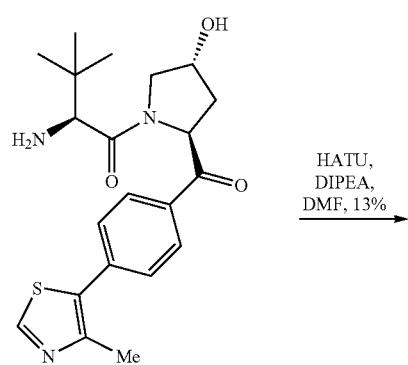

-continued
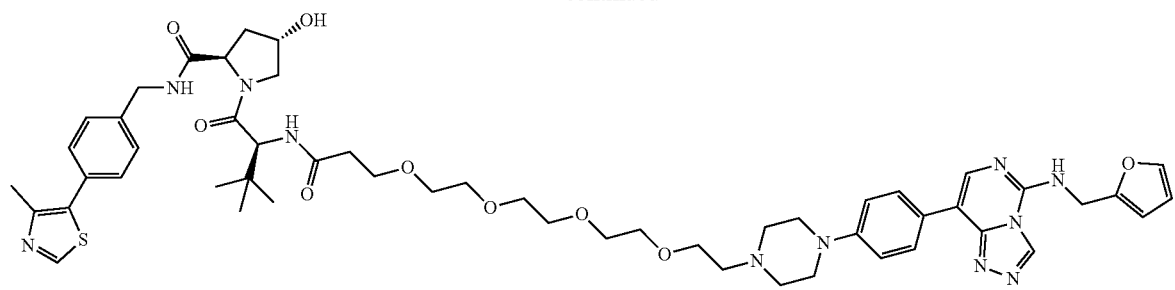
NUCC-0203227
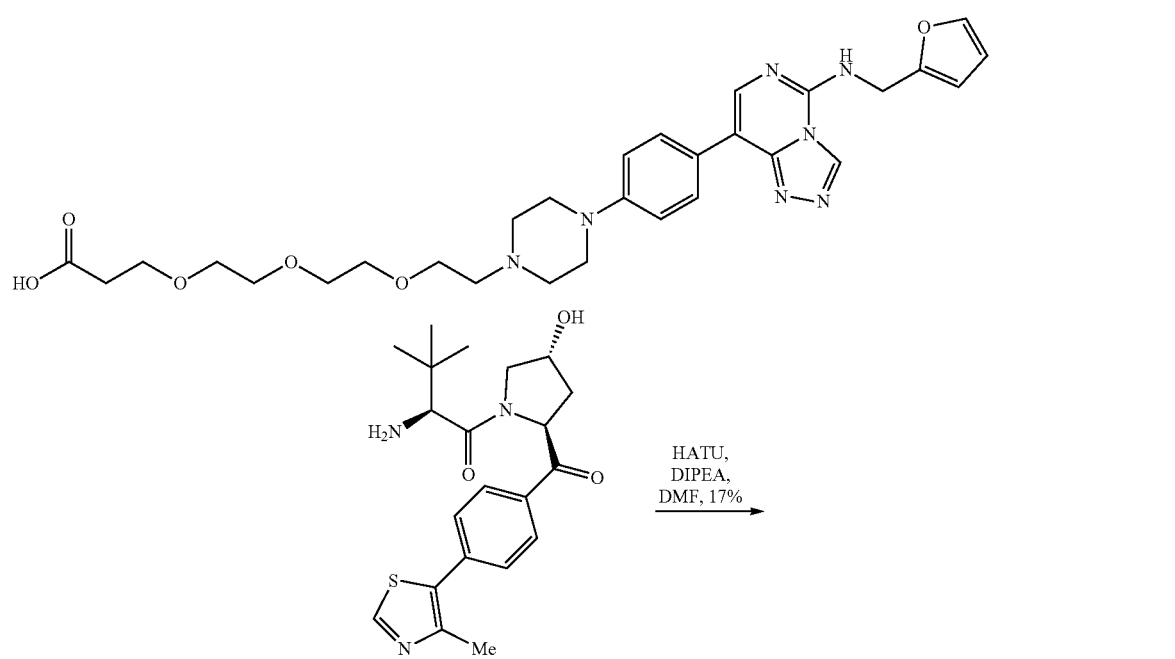
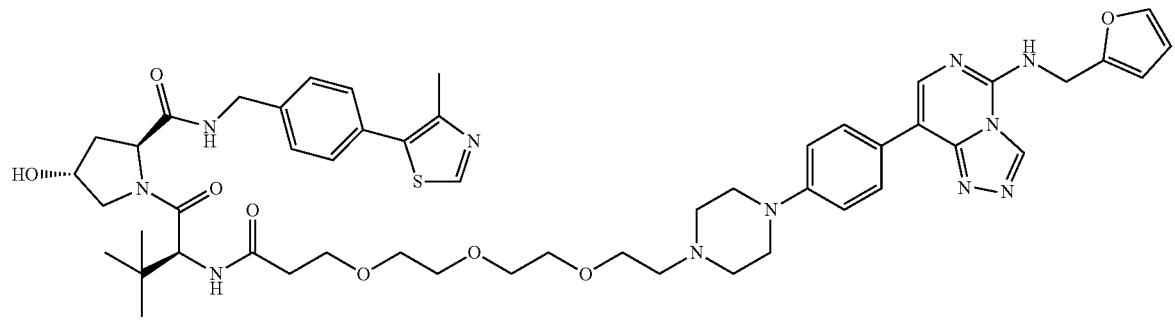
NUCC-0203226
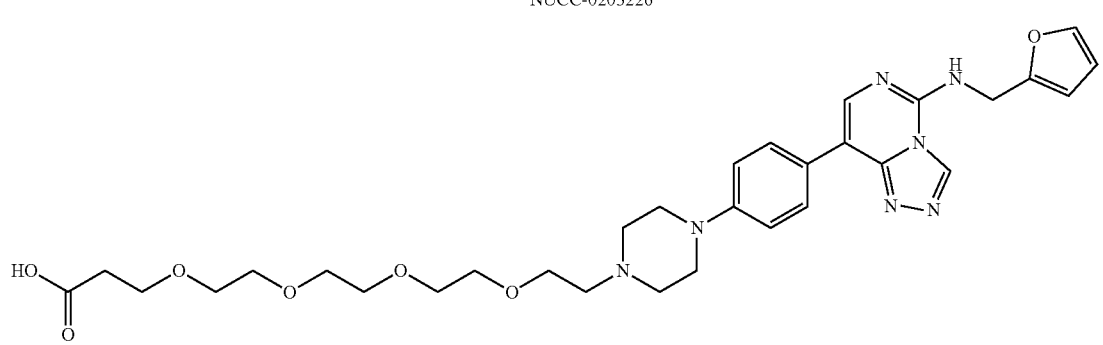

-continued
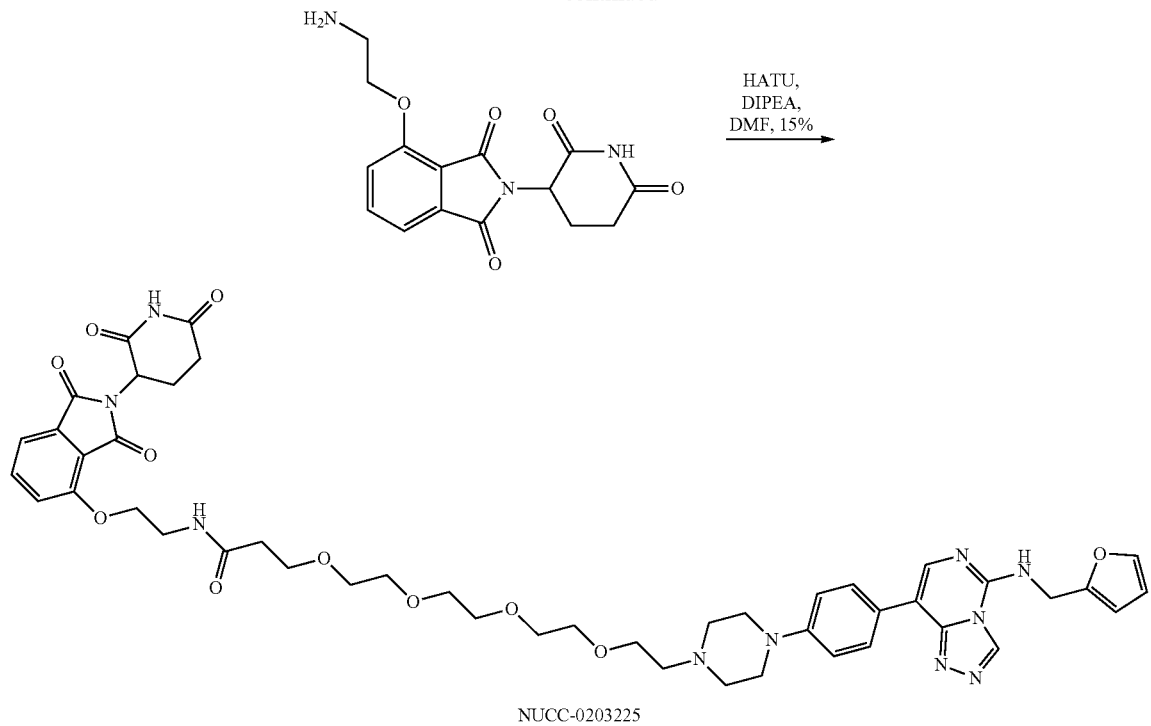
NUCC-0203225
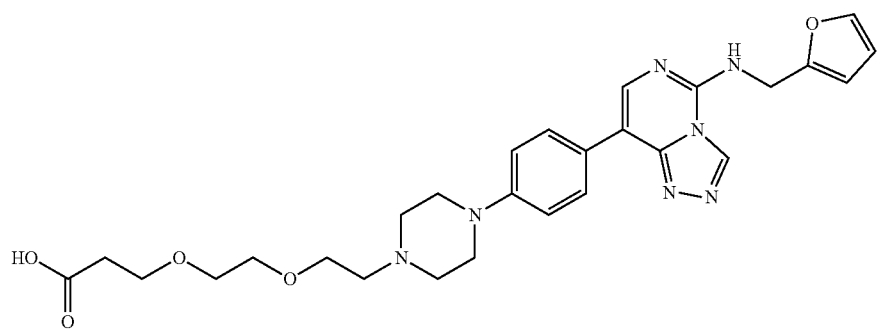
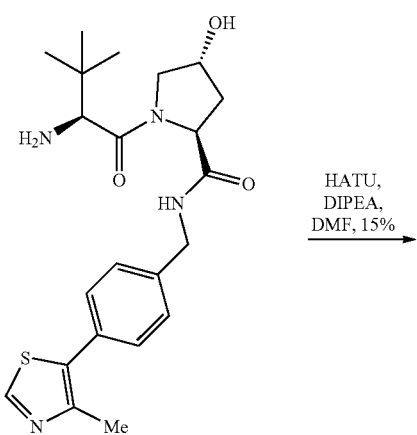

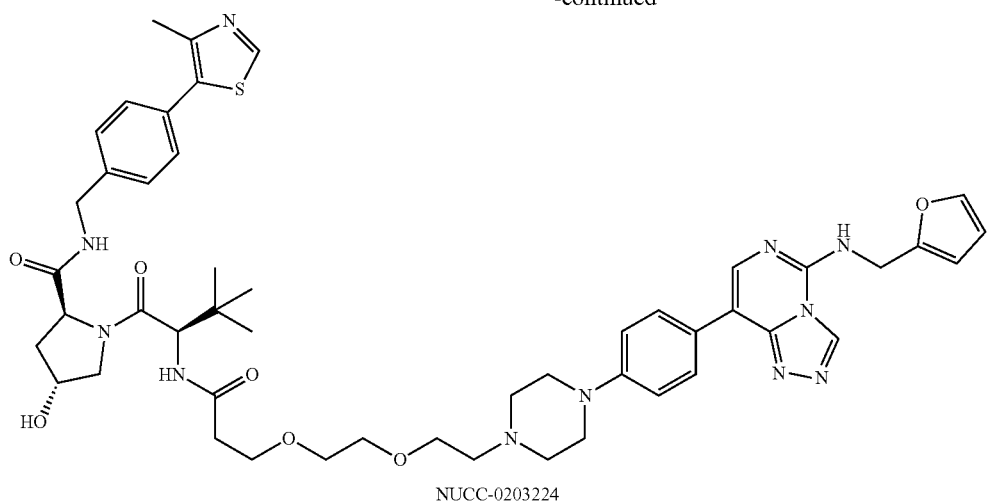
NUCC-0203224
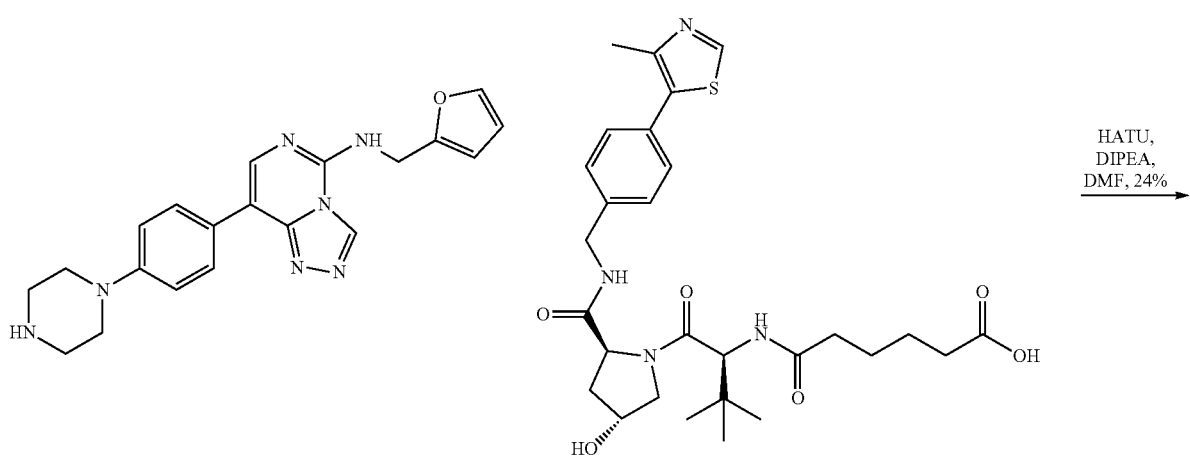
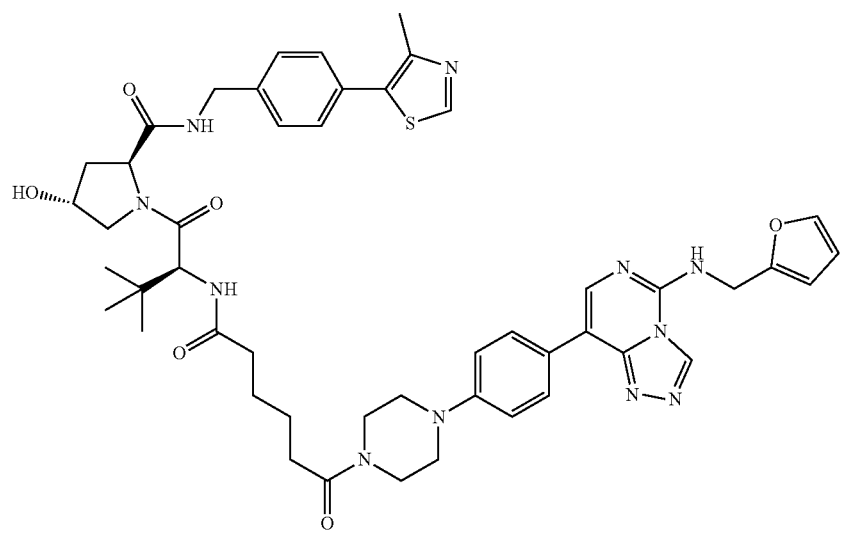
NUCC-0203222

-continued
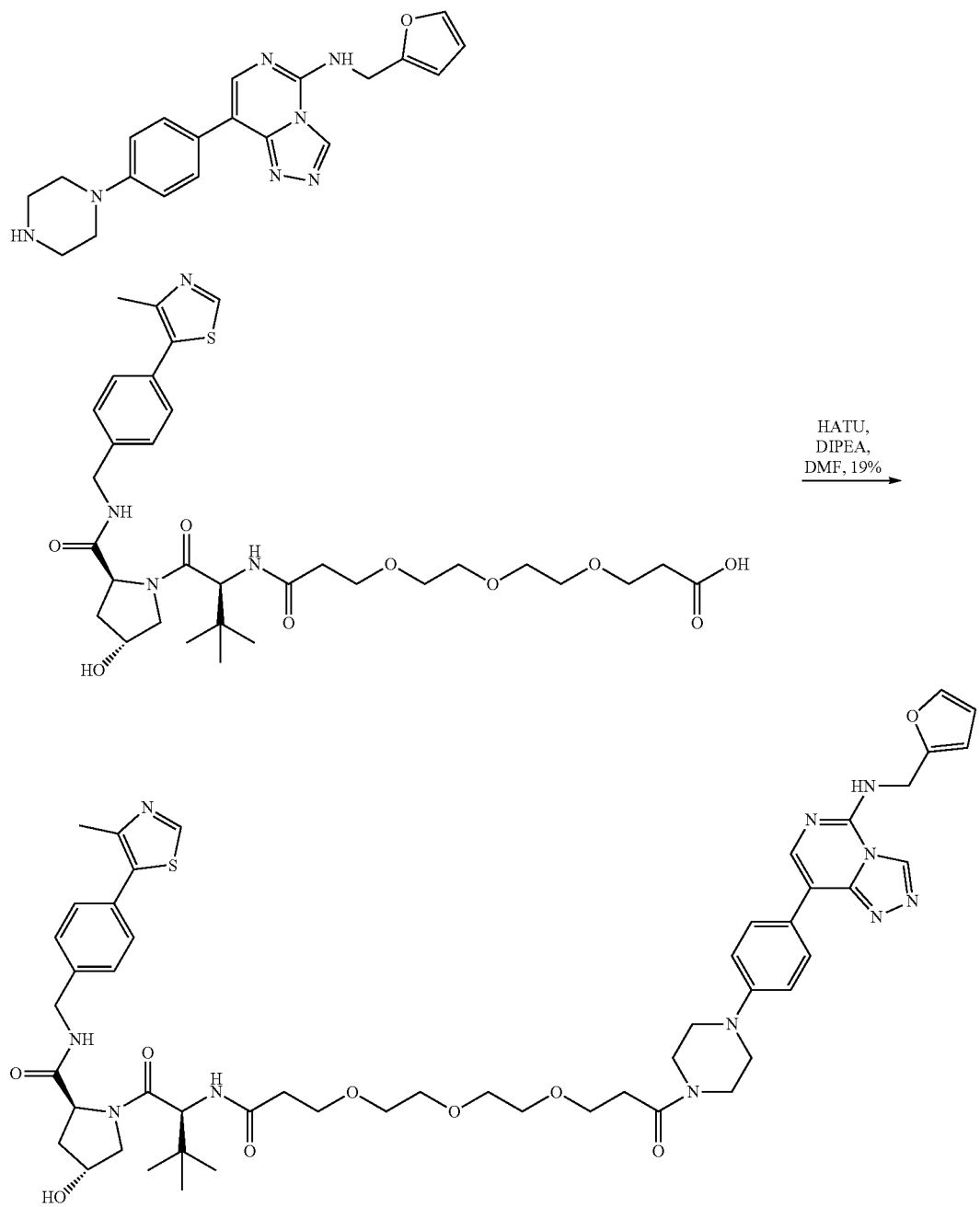
NUCC-0203221
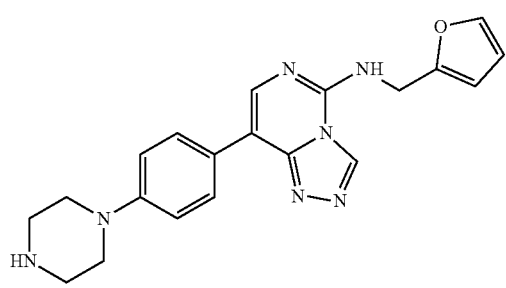

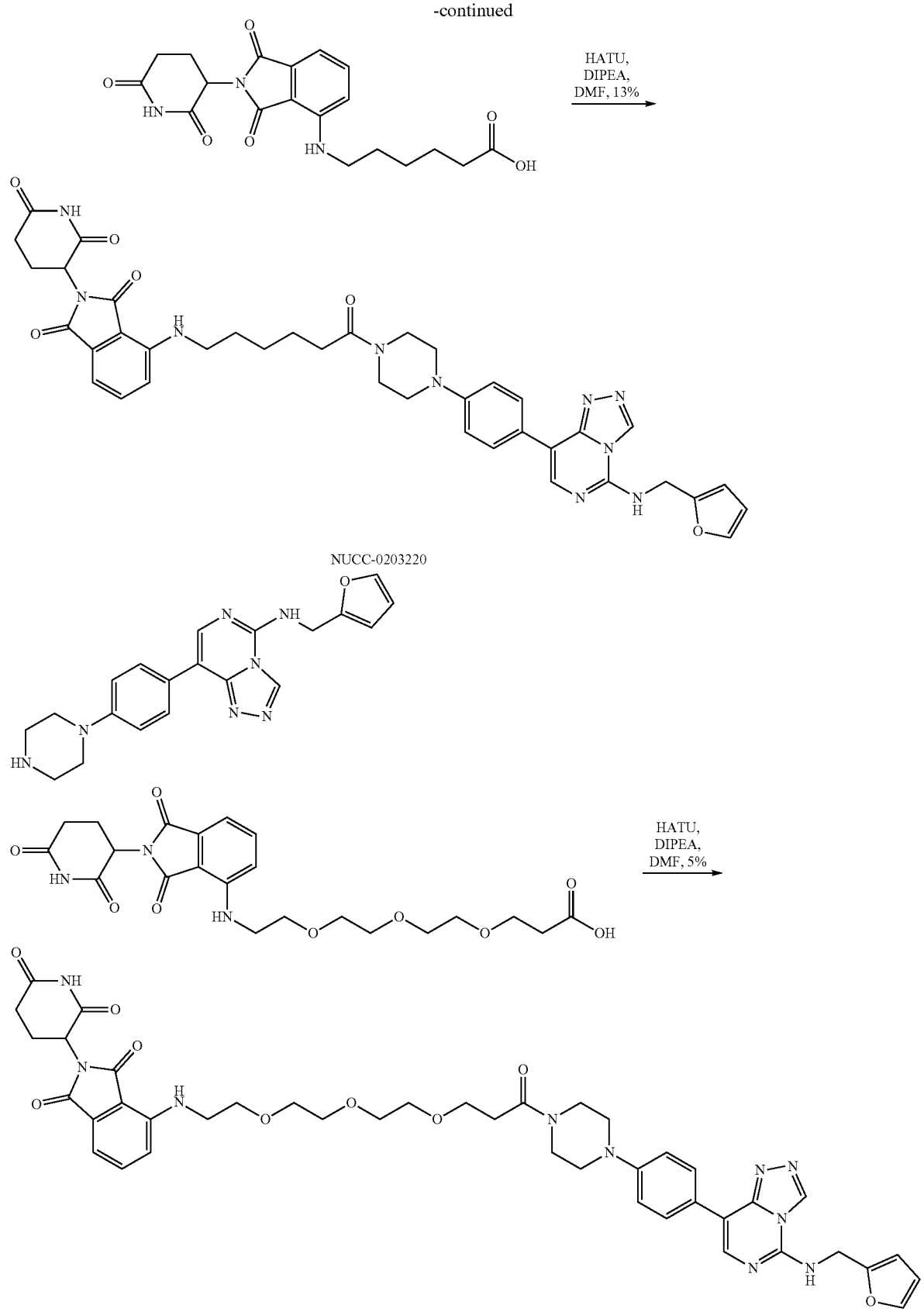

Table of Compounds
| Compound Name | Structure |
|---|---|
| NUCC-0226131 | 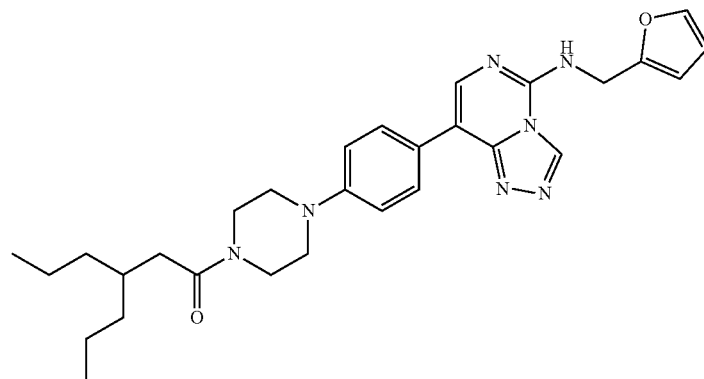 |
| NUCC-0226130 | 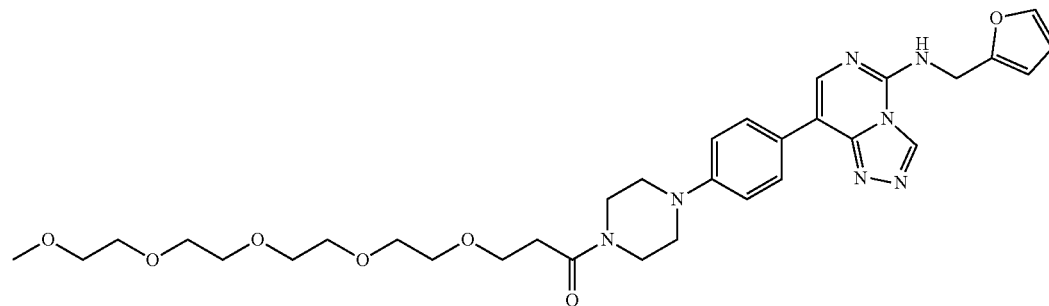 [SMILES: COCCOCCOCCOCCOCCC(=O)N1CCN(c2ccc(-c3cnc(NCc4ccco4)n4cnnc34)cc2)CC1] |
| NUCC-0226129 | 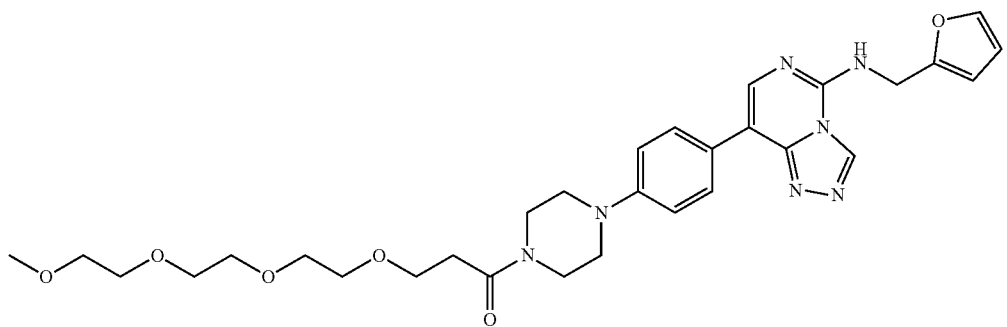 [SMILES: COCCOCCOCCOCCC(=O)N1CCN(c2ccc(-c3cnc(NCc4ccco4)n4cnnc34)cc2)CC1] |
| NUCC-0226128 | 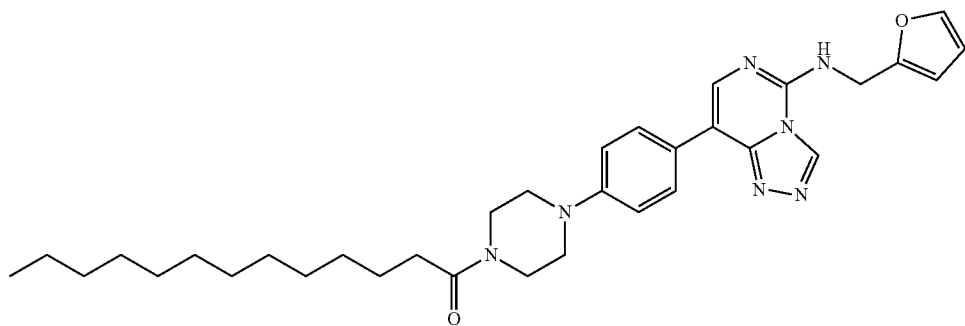 [SMILES: CCCCCCCCCCCCC(=O)N1CCN(c2ccc(-c3cnc(NCc4ccco4)n4cnnc34)cc2)CC1] |

Table of Compounds
| Compound Name | Structure |
|---|---|
| NUCC-0226127 | 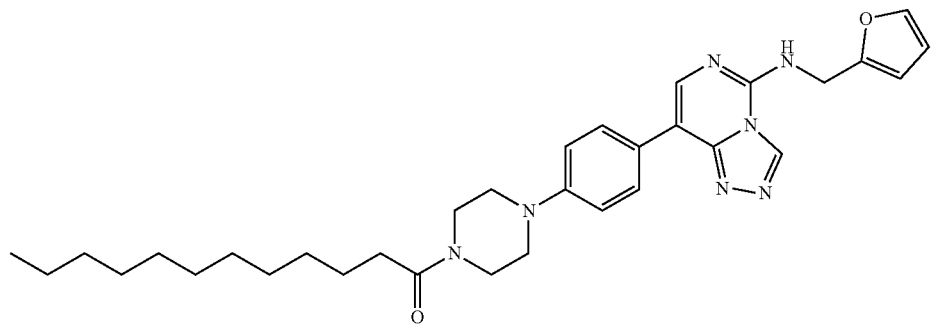 [SMILES: CCCCCCCCCCCC(=O)N1CCN(c2ccc(-c3cnc(NCc4ccco4)n4cnnc34)cc2)CC1] |
| NUCC-0226126 | 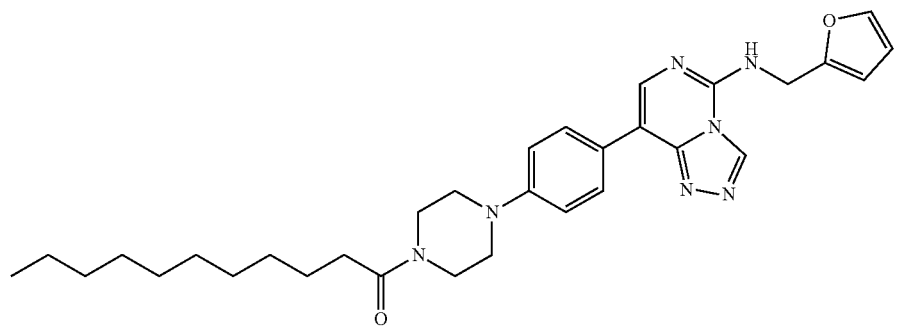 [SMILES: CCCCCCCCCCC(=O)N1CCN(c2ccc(-c3cnc(NCc4ccco4)n4cnnc34)cc2)CC1] |
| NUCC-0226125 | 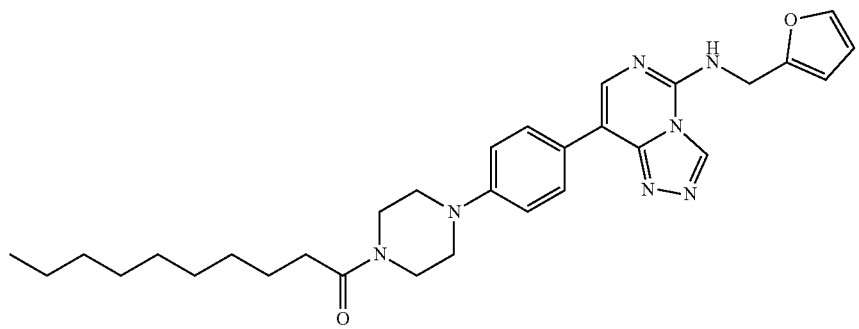 [SMILES: CCCCCCCCCC(=O)N1CCN(c2ccc(-c3cnc(NCc4ccco4)n4cnnc34)cc2)CC1] |
| NUCC-0226124 | 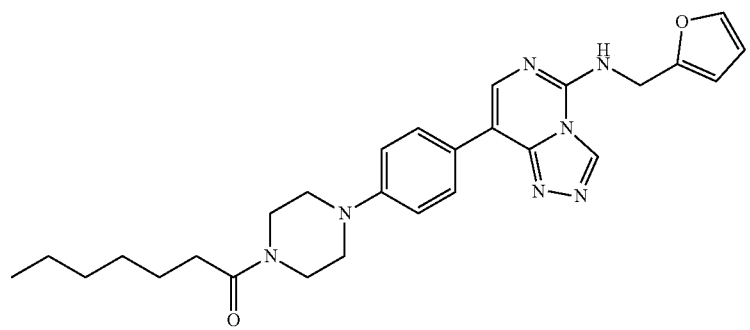 [SMILES: CCCCCCC(=O)N1CCN(c2ccc(-c3cnc(NCc4ccco4)n4cnnc34)cc2)CC1] |

-continued
Table of Compounds
| Compound Name | Structure |
|---|---|
| NUCC-0226123 | 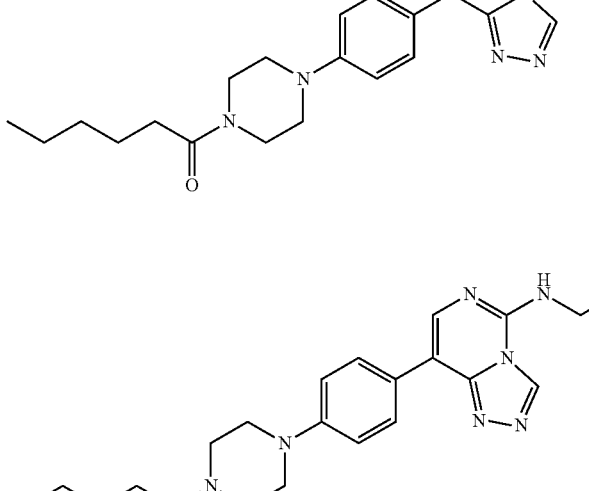 |
| NUCC-0226122 | 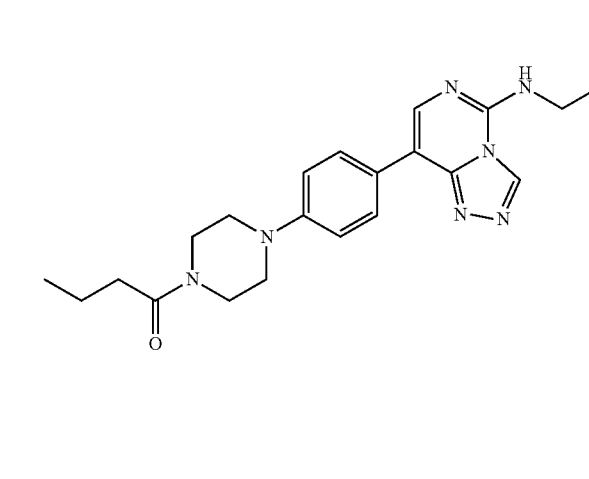 |
| NUCC-0226121 | 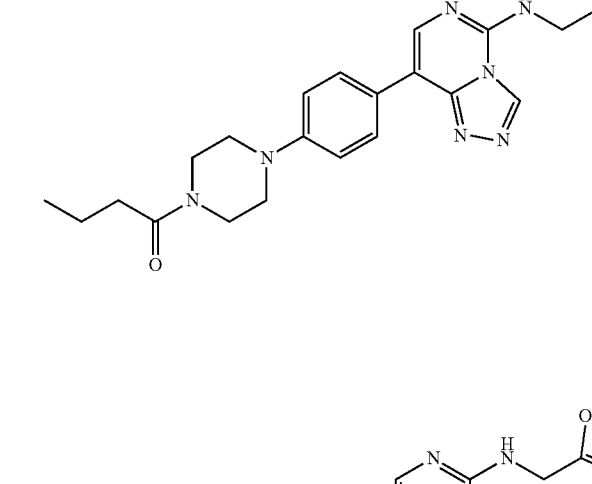 |
| NUCC-0226120 | 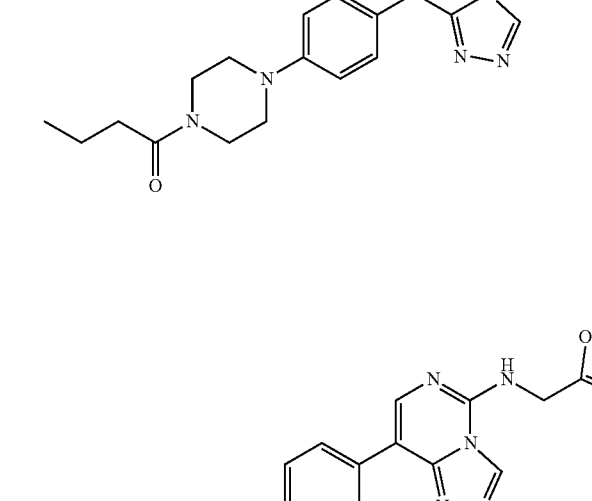 |

-continued

Table of Compounds

| Compound Name | Structure |
|---|---|
| NUCC-0223591 | 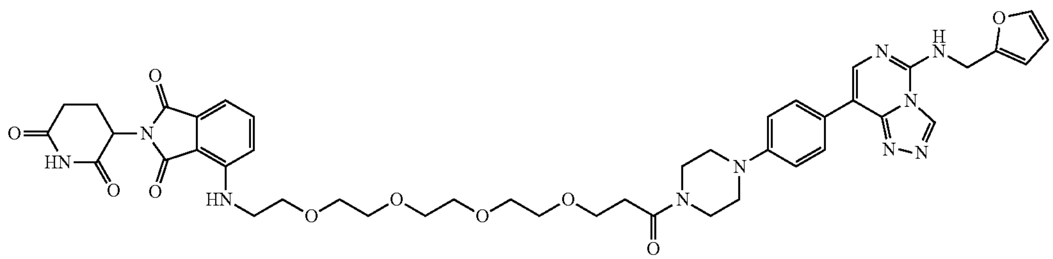 [SMILES: O=C1CCC(N2C(=O)c3cccc(NCCOCCOCCOCCOCCC(=O)N4CCN(c5ccc(-c6cnc(NCc7ccco7)n7cnnc67)cc5)CC4)c3C2=O)C(=O)N1] |
| NUCC-0223590 | 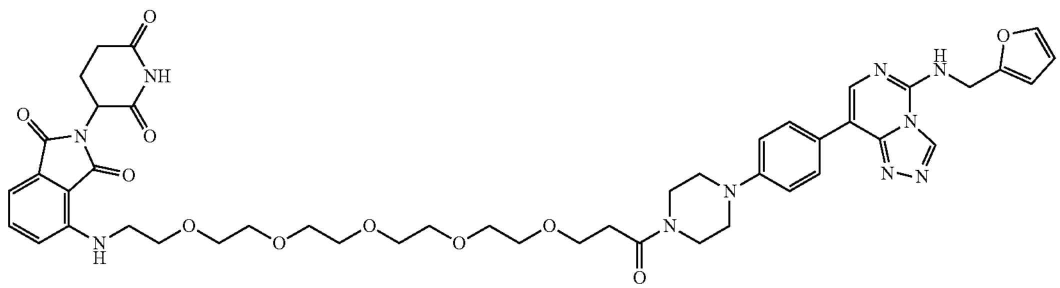 [SMILES: O=C1CCC(N2C(=O)c3cccc(NCCOCCOCCOCCOCCOCCC(=O)N4CCN(c5ccc(-c6cnc(NCc7ccco7)n7cnnc67)cc5)CC4)c3C2=O)C(=O)N1] |
| NUCC-0223589 | 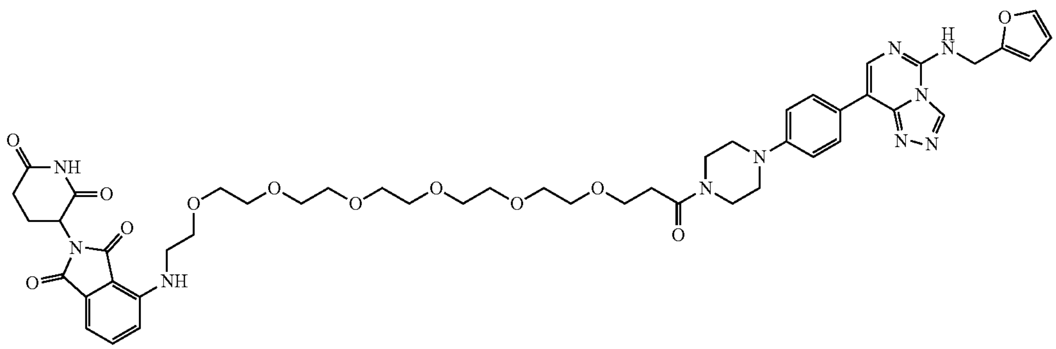 [SMILES: O=C1CCC(N2C(=O)c3cccc(NCCOCCOCCOCCOCCOCCOCCC(=O)N4CCN(c5ccc(-c6cnc(NCc7ccco7)n7cnnc67)cc5)CC4)c3C2=O)C(=O)N1] |
| NUCC-0223588 | 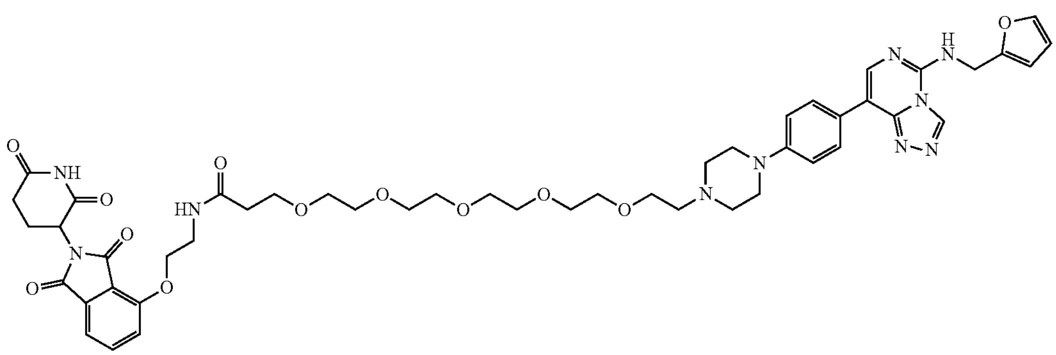 [SMILES: O=C(CCOCCOCCOCCOCCOCCN1CCN(c2ccc(-c3cnc(NCc4ccco4)n4cnnc34)cc2)CC1)NCCOc1cccc2c1C(=O)N(C1CCC(=O)NC1=O)C2=O] |

-continued
Table of Compounds
| Compound Name | Structure |
|---|---|
| NUCC-0223587 | 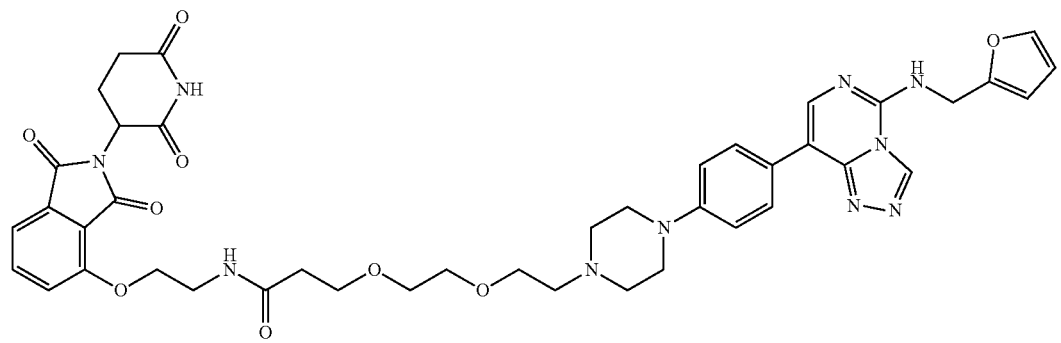 [SMILES: O=C(CCOCCOCCN1CCN(c2ccc(-c3cnc(NCc4ccco4)n4cnnc34)cc2)CC1)NCCOc1cccc2c1C(=O)N(C1CCC(=O)NC1=O)C2=O] |
| NUCC-0223586 | 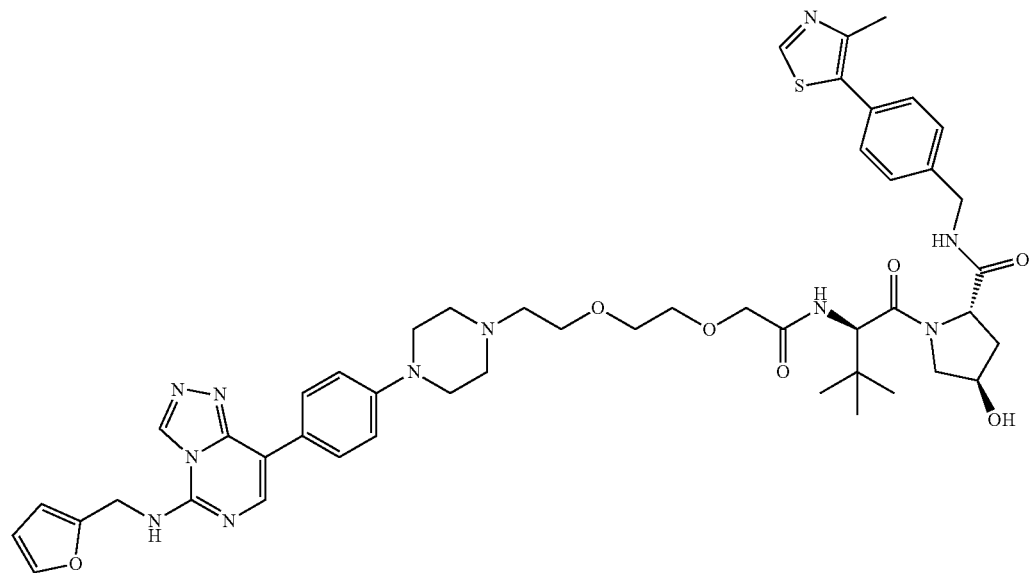 [SMILES: Cc1ncsc1-c1ccc(CNC(=O)[C@@H]2C[C@@H](O)CN2C(=O)[C@H](NC(=O)COCCOCCN2CCN(c3ccc(-c4cnc(NCc5ccco5)n5cnnc45)cc3)CC2)C(C)(C)C)cc1] |
| NUCC-0223585 | 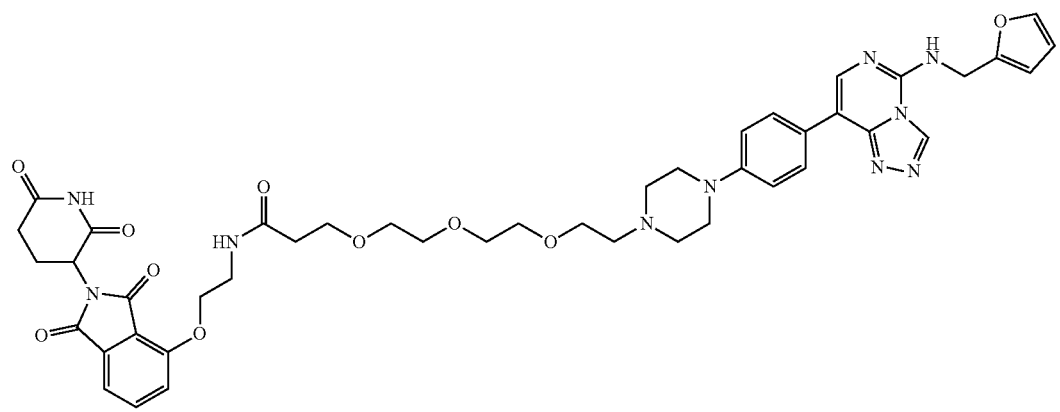 [SMILES: O=C(CCOCCOCCOCCN1CCN(c2ccc(-c3cnc(NCc4ccco4)n4cnnc34)cc2)CC1)NCCOc1cccc2c1C(=O)N(C1CCC(=O)NC1=O)C2=O] |

| Compound Name | Structure |
|---|---|
| NUCC-0203229 | 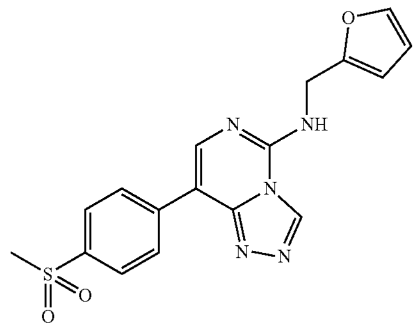 [SMILES: CS(=O)(=O)c1ccc(-c2cnc(NCc3ccco3)n3cnnc23)cc1] |
| NUCC-0203228 | 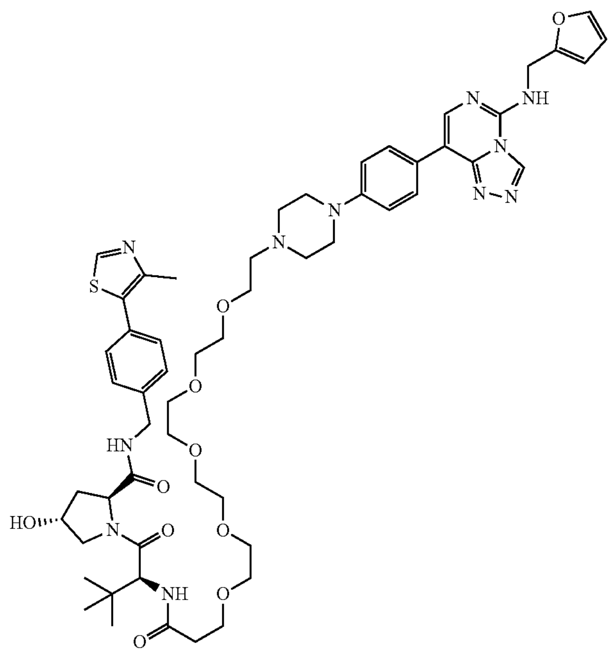 [SMILES: Cc1ncsc1-c1ccc(CNC(=O)[C@@H]2C[C@@H](O)CN2C(=O)[C@@H](NC(=O)CCOCCOCCOCCOCCOCCN2CCN(c3ccc(-c4cnc(NCc5ccco5)n5cnnc45)cc3)CC2)C(C)(C)C)cc1] |
| NUCC-0203227 | 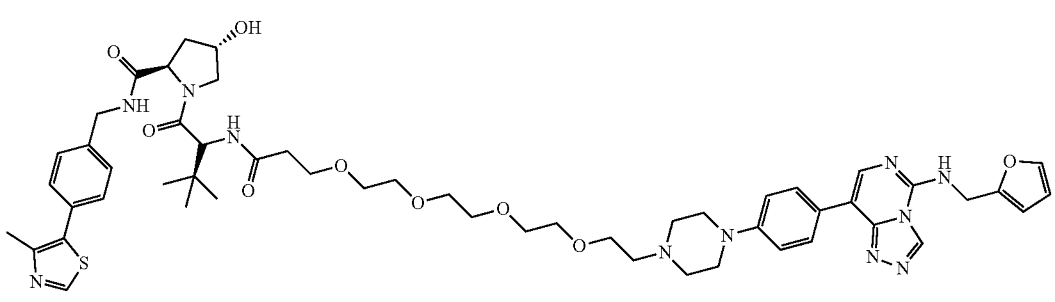 |
| NUCC-0203226 | 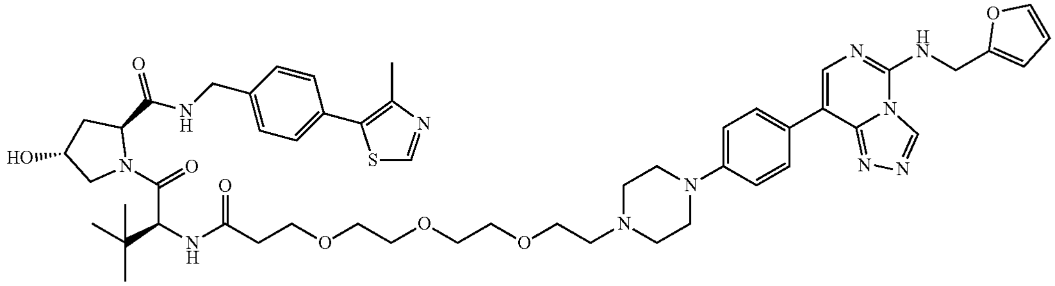 [SMILES: Cc1ncsc1-c1ccc(CNC(=O)[C@@H]2C[C@@H](O)CN2C(=O)[C@@H](NC(=O)CCOCCOCCOCCN2CCN(c3ccc(-c4cnc(NCc5ccco5)n5cnnc45)cc3)CC2)C(C)(C)C)cc1] |

|  |  |
|---|---|
| Compound Name | Structure |
| NUCC-0203225 | 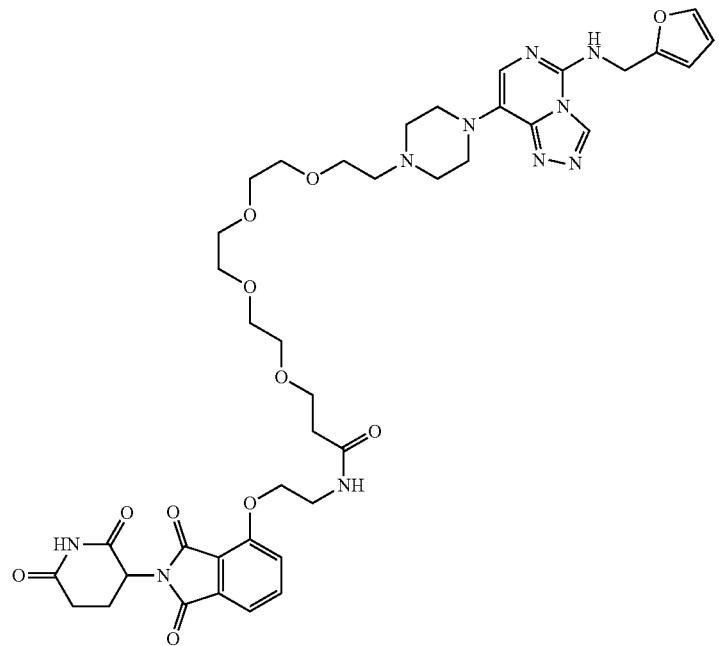 [SMILES: O=C(CCOCCOCCOCCOCCN1CCN(c2cnc(NCc3ccco3)n3cnnc23)CC1)NCCOc1cccc2c1C(=O)N(C1CCC(=O)NC1=O)C2=O] |
| NUCC-0203224 | 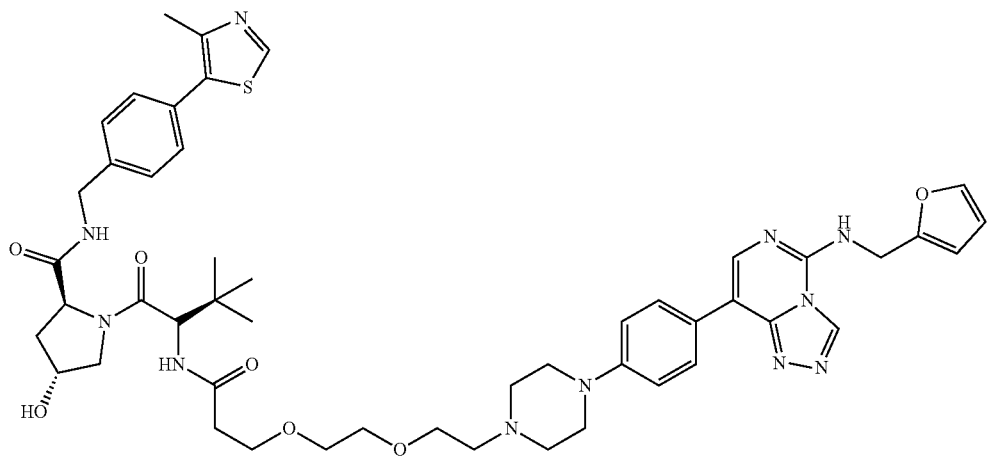 |

-continued
Table of Compounds
| Compound Name | Structure |
|---|---|
| NUCC-0203222 | 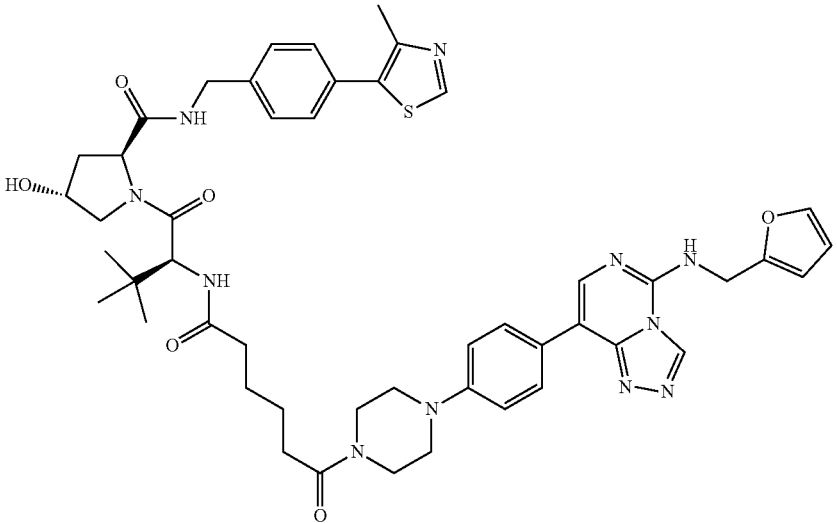 [SMILES: Cc1ncsc1-c1ccc(CNC(=O)[C@@H]2C[C@@H](O)CN2C(=O)[C@@H](NC(=O)CCCCC(=O)N2CCN(c3ccc(-c4cnc(NCc5ccco5)n5cnnc45)cc3)CC2)C(C)(C)C)cc1] |
| NUCC-0203221 | 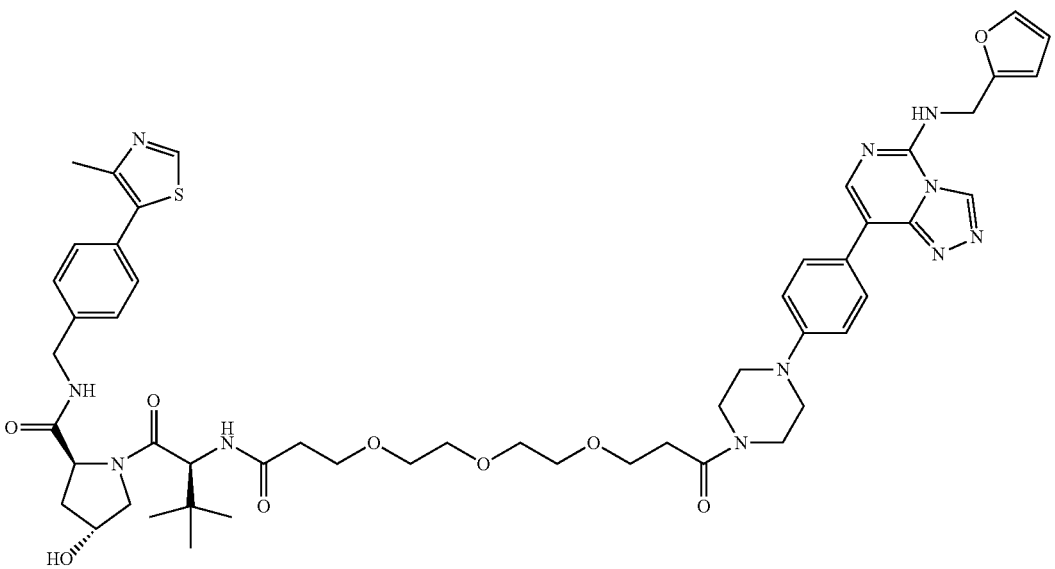 [SMILES: Cc1ncsc1-c1ccc(CNC(=O)[C@@H]2C[C@@H](O)CN2C(=O)[C@@H](NC(=O)CCOCCOCCOCCC(=O)N2CCN(c3ccc(-c4cnc(NCc5ccco5)n5cnnc45)cc3)CC2)C(C)(C)C)cc1] |
| NUCC-0203220 | 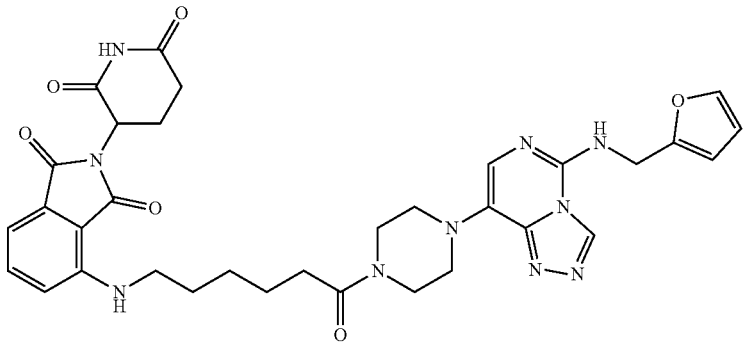 [SMILES: O=C1CCC(N2C(=O)c3cccc(NCCCCCC(=O)N4CCN(c5cnc(NCc6ccco6)n6cnnc56)CC4)c3C2=O)C(=O)N1] |

Table of Compounds

| Compound Name | Structure |
|---|---|
| NUCC-0203219 | (structure shown) |

Example 2—Activity of Compounds Described Herein

Figure 2:
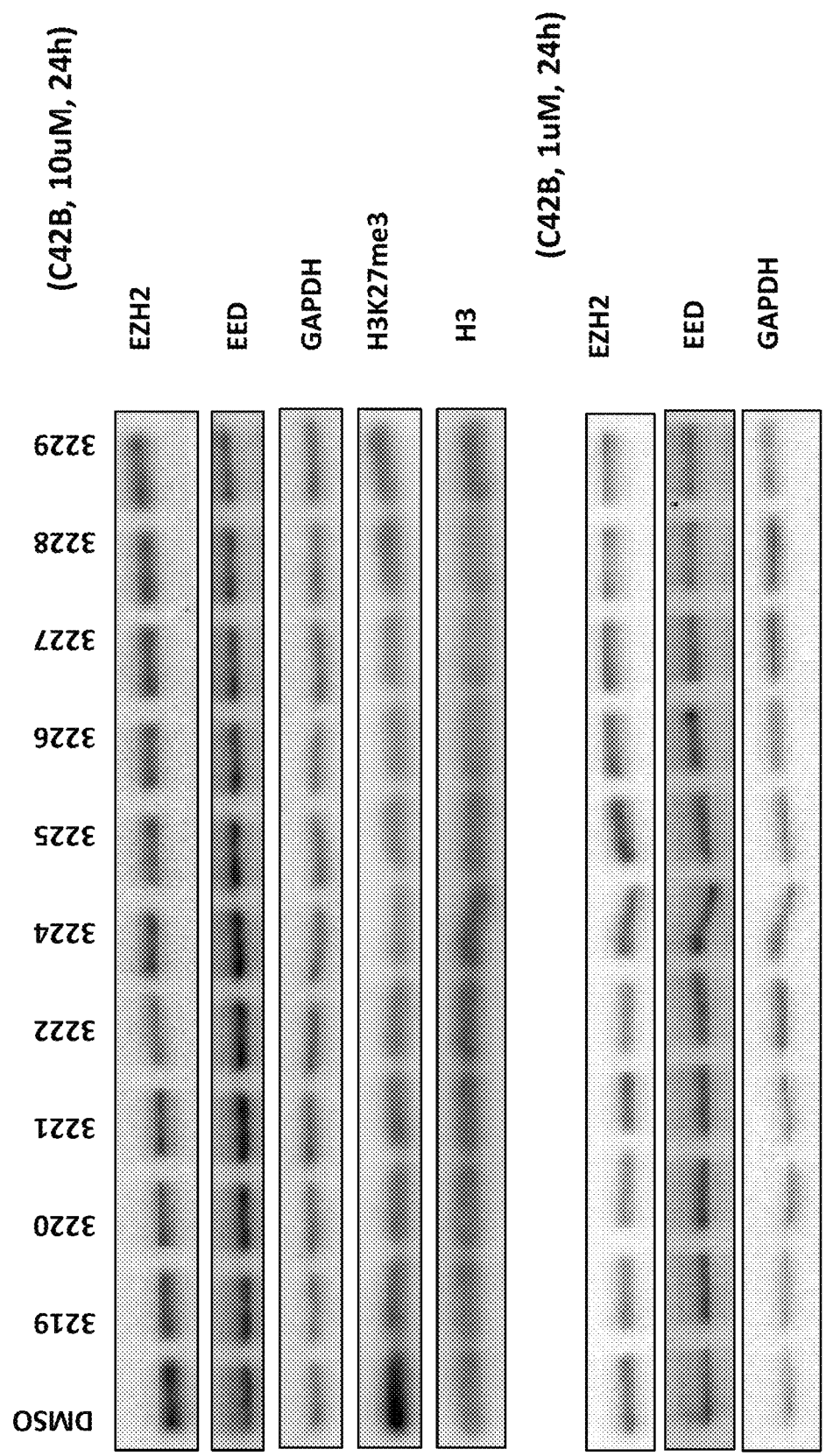
FIG. 2 shows WB comparing of activity of compounds 3219, 3220, 3221, 3222, 3224, 3225, 3226, 3227, 3228, and 3229 against EZH2, EED, trimethylation of histone H3 lysine 27 (H3k27me3), and histone H3. C4-2B cells were treated with indicated compounds for 24 hours with indicated doses before WB analyses.
Figure 3:
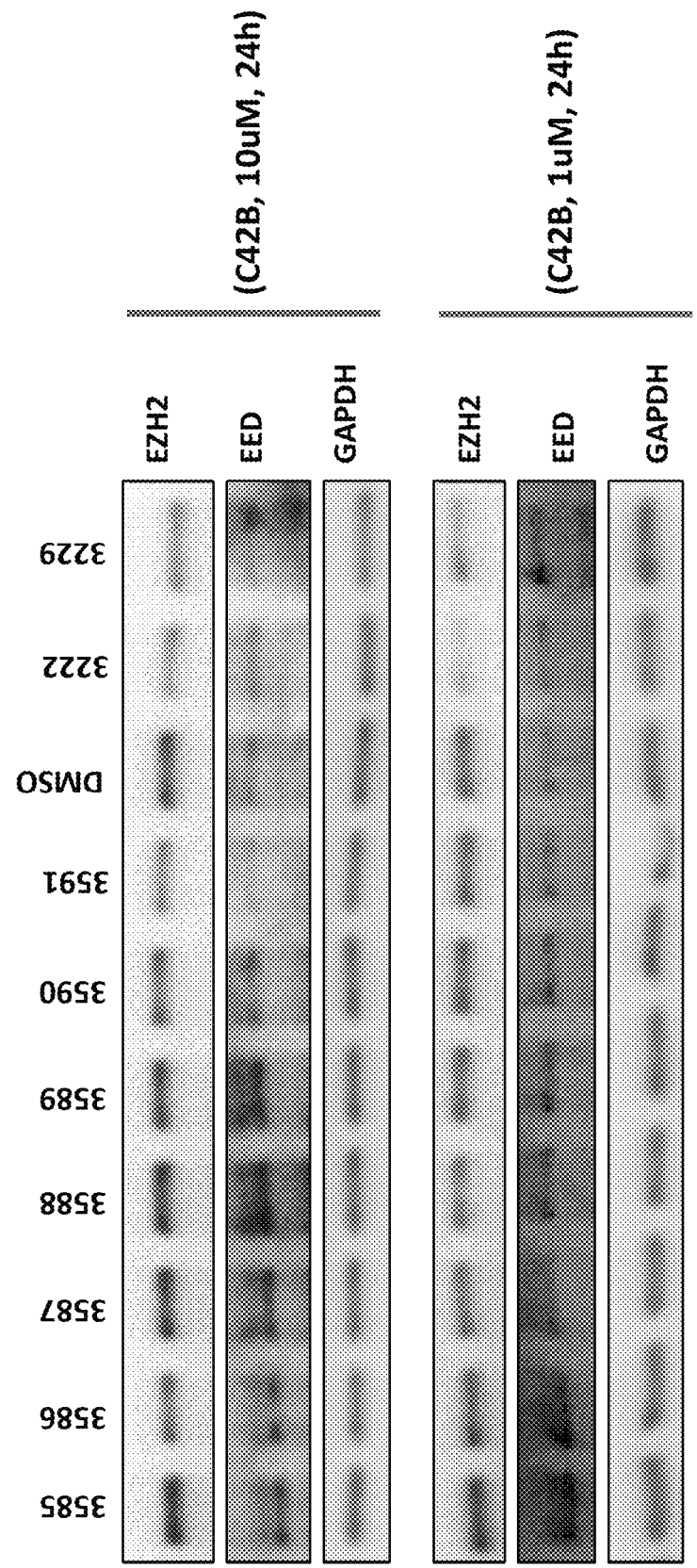
FIG. 3 shows WB comparing of activity of compounds 3585, 3586, 3587, 3588, 3590, 3591, 3222, and 3229 against EZH2 and EED. C4-2B cells were treated with indicated compounds for 24 hours with indicated doses before WB analyses.
Figure 4:
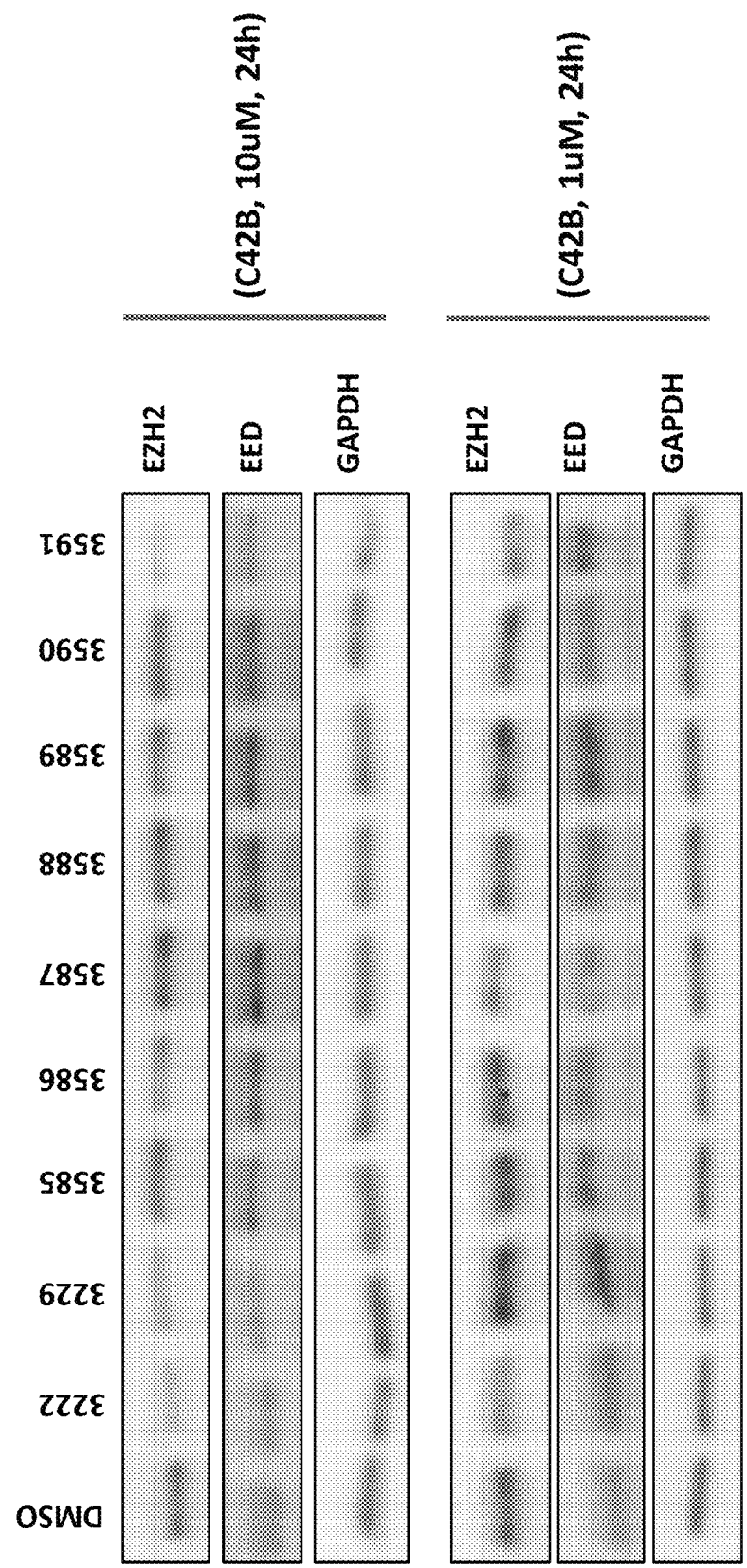
FIG. 4 shows WB comparing of activity of compounds 3222, 3229, 3585, 3586, 3587, 3588, 3589, 3590, and 3591 against EZH2 and EED. C4-213 cells were treated with indicated compounds for 24 hours with indicated doses before WB analyses.

FIGS. 1-4 demonstrate the activity of the presently disclosed compounds against several different proteins, including EZH2, EED, histone H3, and trimethylation of histone H3 lysine 27 (113k27me3). FIGS. 1-4 show western blots (WB) of cells treated with the indicated compounds under the conditions shown in the figures.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. The cited references are incorporated by reference herein in their entireties. In the event that there is an inconsistency between a definition of a term in the specification as compared to a definition of the term in a cited reference, the term should be interpreted based on the definition in the specification.

We claim:
1. A compound of the following formula:

$$M_{EED}\text{-L-}M_{E3}$$

or a pharmaceutically acceptable salt or stereoisomer thereof,
wherein:
$M_{EED}$ is Formula II:

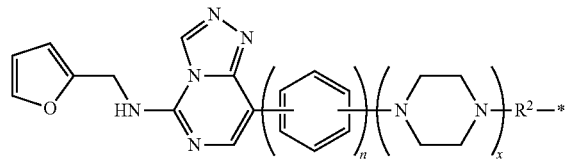

II wherein:
n is 1;
x is 1;
$R^2$ is a bond or —C(O)—; and
* is the point of attachment to the —CH$_2$— of the —(CH$_2$CH$_2$O)$_n$— of L;

(i) L is a linker of the following formula:

*—(CH$_2$CH$_2$O)$_n$CH$_2$CH$_2$-+ wherein:
n is 3, 4, 5, 6, 7, 8, 9, 10, 11, 12, 13, 14, 15, 16, 17, 18, 19, or 20;

* is the point of attachment to the piperazinylene nitrogen atom or —C(O)— of M$_{EED}$; and
+ is the point of attachment to the —C(O)—, —NH—, or —O— of M$_{E3}$; or (ii) L is a linker of the following formula:

wherein:
n is 1, 2, 3, 4, 5, 6, 7, 8, 9, 10, 11, 12, 13, 14, 15, 16, 17, 18, 19, or 20;
* is the point of attachment to the piperazinylene nitrogen atom or —C(O)— of M$_{EED}$; and
+ is the point of attachment to the —C(O)—, —NH—, or —O— of M$_{E3}$; and M$_{E3}$ is:

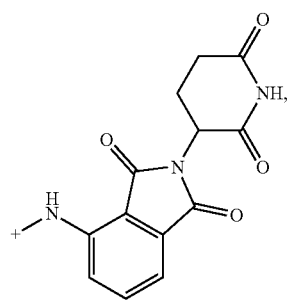

or

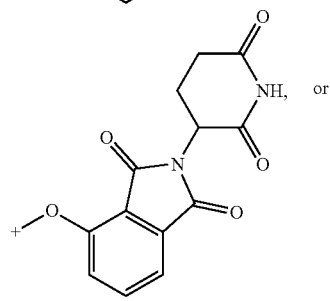

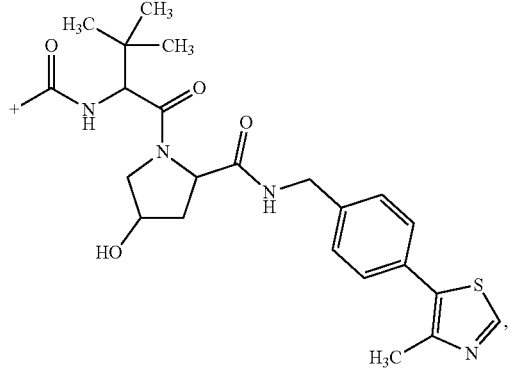

wherein:
+ is the point of attachment to the —CH$_2$— of L.

2. The compound of claim 1, or a pharmaceutically acceptable salt or stereoisomer thereof, wherein M$_{EED}$ is of the following formula:

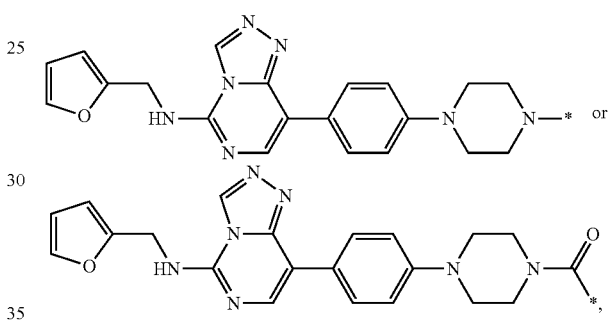

wherein:
* is the point of attachment to the —CH$_2$— of the —(CH$_2$CH$_2$O)$_n$— of L.

3. The compound of claim 1, or a stereoisomer thereof, wherein the compound, or stereoisomer thereof, is selected from the group consisting of:

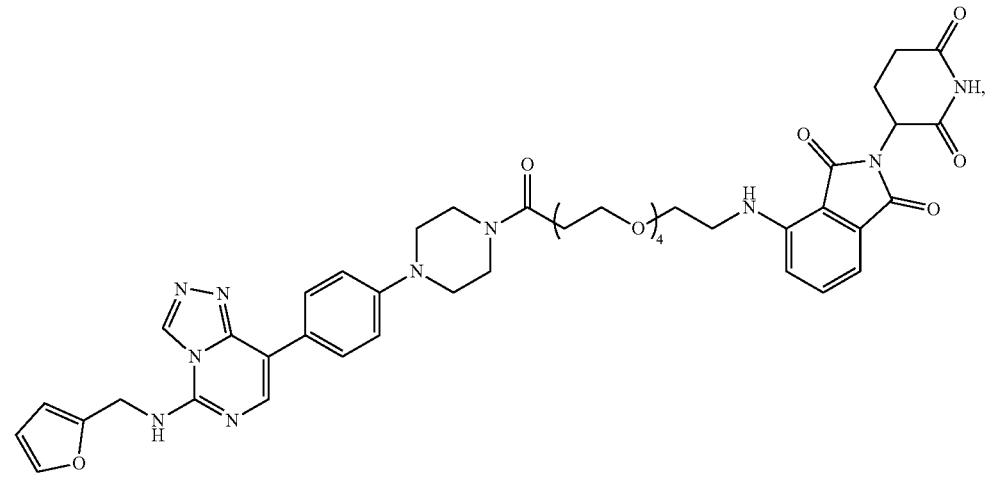

-continued
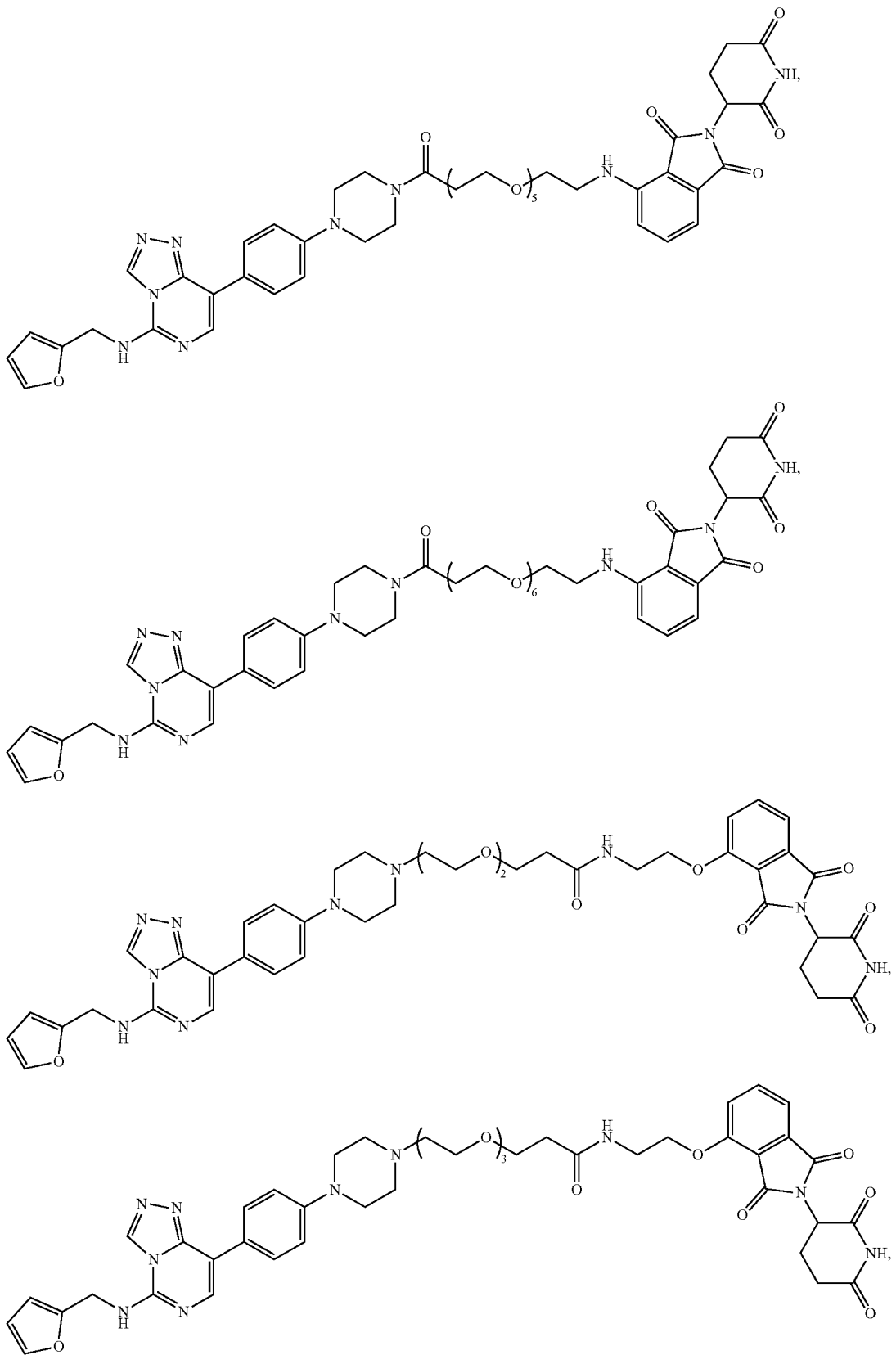

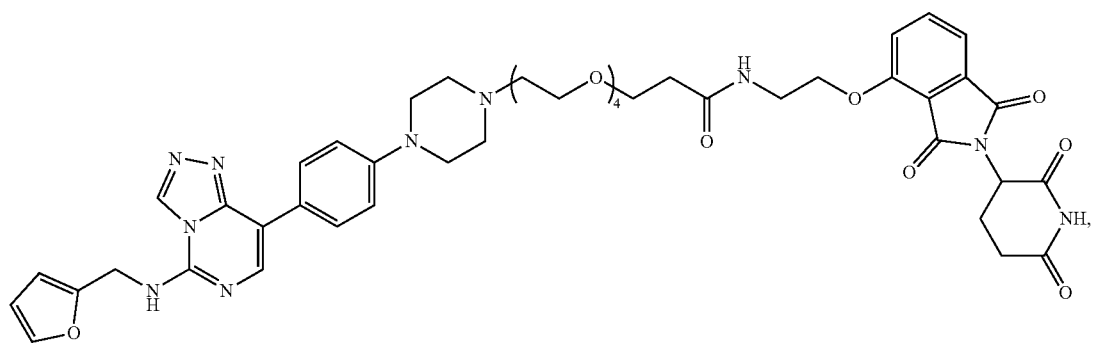
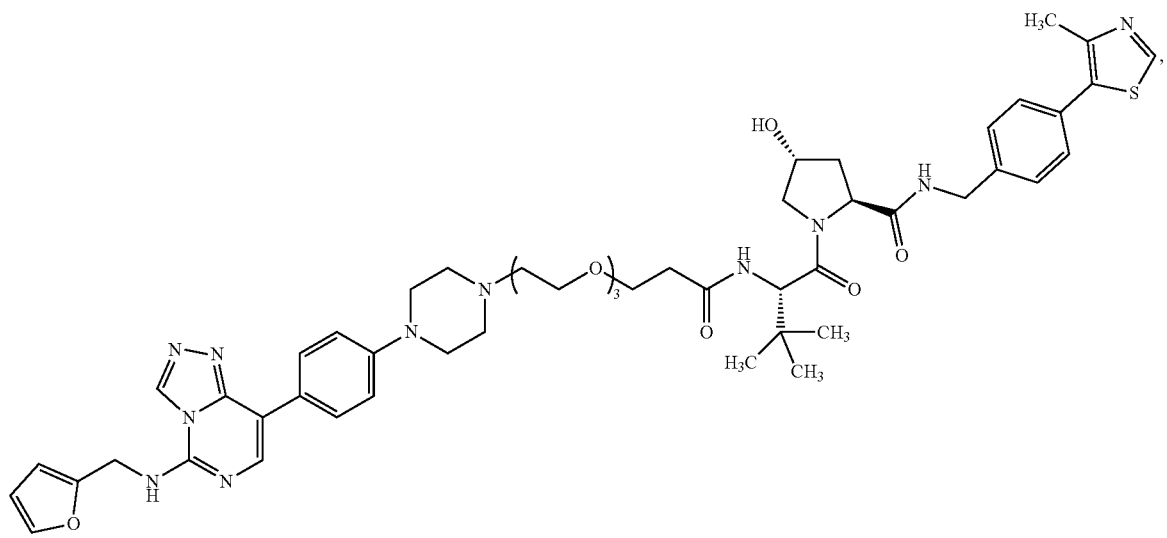
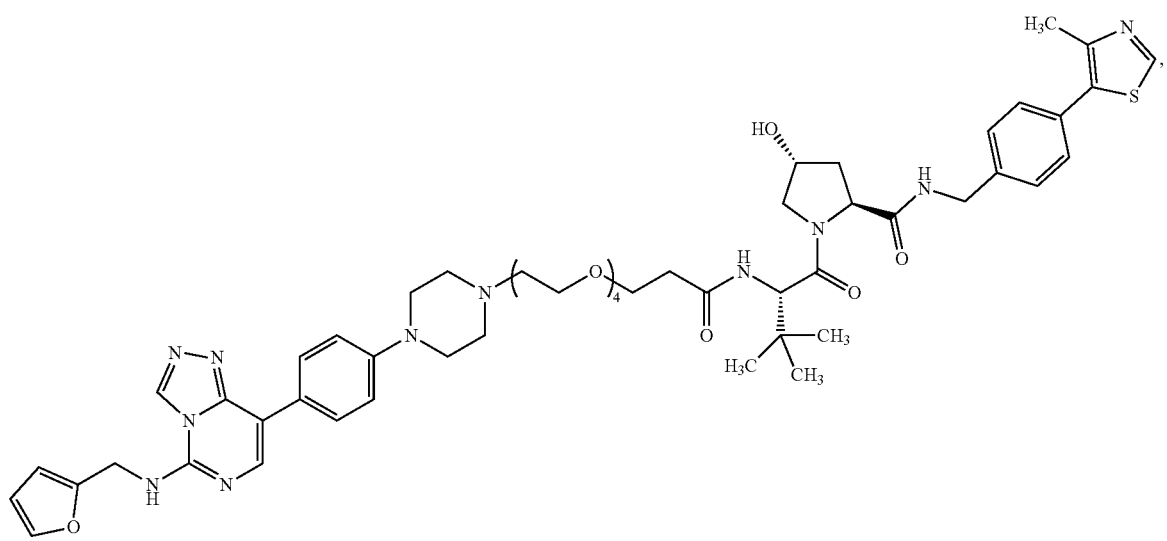

-continued
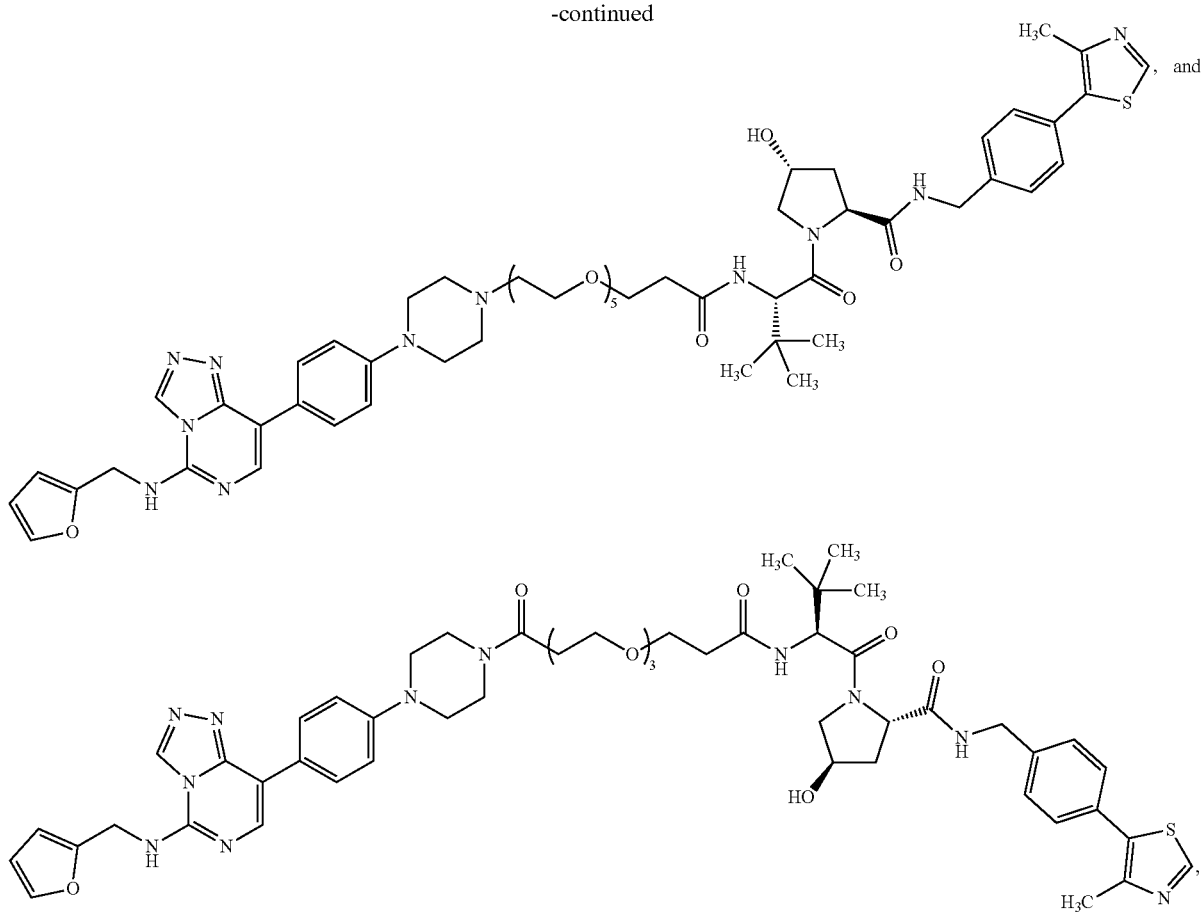
or a pharmaceutically acceptable salt thereof.
4. A pharmaceutical composition comprising a pharmaceutically acceptable carrier, excipient, or diluent and a compound of claim 1, or a pharmaceutically acceptable salt or stereoisomer thereof.
* * * * *